(12) United States Patent
Bogdanov et al.

(10) Patent No.: US 8,084,589 B2
(45) Date of Patent: Dec. 27, 2011

(54) PHOSPHORAMIDITE NUCLEOSIDE ANALOGS

(75) Inventors: Alexei Bogdanov, Westborough, MA (US); Valeriy Metelev, Moscow (RU); David Tabatadze, Worcester, MA (US); Paul Zamecnik, Boston, MA (US)

(73) Assignees: University of Massachusetts, Shrewsbury, MA (US); The General Hospital Corporation Massachusetts, Boston, MA (US)

( * ) Notice: Subject to any disclaimer, the term of this patent is extended or adjusted under 35 U.S.C. 154(b) by 88 days.

(21) Appl. No.: 12/201,758

(22) Filed: Aug. 29, 2008

(65) Prior Publication Data
US 2009/0136940 A1    May 28, 2009

Related U.S. Application Data

(60) Provisional application No. 60/967,184, filed on Aug. 31, 2007.

(51) Int. Cl.
*C07G 3/00* (2006.01)
*C07H 21/02* (2006.01)
*C07H 21/00* (2006.01)
*A61K 48/00* (2006.01)
*G01N 33/53* (2006.01)

(52) U.S. Cl. ...... 536/4.1; 536/23.1; 536/25.3; 536/25.4; 514/44; 435/7.1

(58) Field of Classification Search ............. 536/4.1, 536/23.1, 25.3, 25.4; 514/44; 435/7.1
See application file for complete search history.

(56) References Cited

U.S. PATENT DOCUMENTS

| | | | |
|---|---|---|---|
| 5,646,261 | A | 7/1997 | Uhlmann et al. |
| 5,700,919 | A | 12/1997 | Seliger et al. |
| 5,902,878 | A | 5/1999 | Seliger et al. |
| 5,998,603 | A | 12/1999 | Cook et al. |
| 6,312,906 | B1 | 11/2001 | Cass et al. |
| 6,331,632 | B1 | 12/2001 | Reedy et al. |
| 6,727,356 | B1 | 4/2004 | Reed et al. |
| 7,258,974 | B2 | 8/2007 | Chou |
| 2003/0036066 | A1 | 2/2003 | Pon et al. |
| 2006/0063147 | A1 | 3/2006 | Chernov et al. |
| 2007/0059690 | A1 | 3/2007 | Islam et al. |

FOREIGN PATENT DOCUMENTS

| WO | WO 01/06016 | * | 1/2001 |
|---|---|---|---|
| WO | WO 2004/113553 | | 12/2004 |

OTHER PUBLICATIONS

Cole et al. Nucleic Acids Research, 2004, vol. 32, No. 11 e86 p. 1-9.*
International Preliminary Report on Patentability issued in International Application No. PCT/US2008/074892, dated Mar. 2, 2010.

(Continued)

*Primary Examiner* — Jezia Riley
(74) *Attorney, Agent, or Firm* — Fish & Richardson P.C.

(57) ABSTRACT

Described are phosphoramidite nucleoside analog monomers, precursors thereof, and oligonucleotides including one or more of the monomers. The monomers can be used during automated synthesis of oligonucleotide derivatives, and allow for incorporation of one or several reporter groups, organic molecules, bio-molecules, small molecules or other chemical groups at the internucleoside phosphotriesters. Oligonucleotides including the monomers have a number of uses in therapeutic, diagnostic, and research applications.

49 Claims, 16 Drawing Sheets

OTHER PUBLICATIONS

Agrawal, S. et al., "Site Specific Functionalization of Oligonucleotides for Attaching Two Different Reporter Groups", Nucleic Acids Research, vol. 18, No. 18, pp. 5419-5423, (1990).

Awad, A. M. et al., "Enzymatic and hybridization properties of oligonucleotide analogs containing novel phosphoramidate internucleotide linkages", Nucleosides Nucleotides & Nucleic Acids, vol. 23, No. 5, pp. 777-787, (2004).

Boutorine, A. S. et al., "Methods of Attaching Unprotected Oligonucleotides to DNA-binding, Fluorescent, or Reactive Ligands for Synthesis of Antisense or Gene-directed Agents and Probes", Molecular Biology, vol. 34, No. 6, pp. 804-813, (2000).

Da Ros, T. et al., "Oligonucleotides and Oligonucleotide Conjugates: A New Approach for Cancer treatment", Current Medicinal Chemistry, vol. 12, No. 1, pp. 71-88, (2005).

Goodchild, J., "Conjugates of Oligonucleotides and Modified Oligonucleotides: A Review of Their Synthesis and Properties", Bioconjugate Chemistry, vol. 1, No. 4, pp. 165-187, (1990).

Guzaev, A. et al., "New Approach for Chemical Phosphorylation of Oligonucleotides at the 5'-Terminus", Tetrahedron, vol. 51, No. 34, pp. 9375-9384, (1995).

Horn, T. et al., "Chemical synthesis and characterization of branched oligodeoxyribonucleotides (bDNA) for use as signal amplifiers in nucleic acid quantification assays", Nucleic Acids Research, vol. 25, No. 23, pp. 4842-4849, (1997).

Markiewicz, W. T. et al., "A new method of synthesis of fluorescently labelled oligonucleotides and their application in DNA sequencing", Nucleic Acids Research, vol. 25, No. 18, pp. 3672-3680, (1997).

Seliger, H. et al., "Specific Intrachain Introduction of Reporter Groups into Oligonucleotides as Substituents at Internucleotidic Linkages", Nucleosides & Nucleotides, vol. 10, No. 1-3, pp. 303-306, (1991).

Silverman, A. P. et al., "Detecting RNA and DNA with Templated Chemical Reactions", Chemical Review, vol. 106, No. 9, pp. 3775-3789, (2006).

Sinha, N. D. et al., "Polymer Support Oligonucleotide Synthesis XVIII: Use of Beta-Cyanoethyl-N,N-Dialkylamino-/N-Morpholino Phosphoramidite of Deoxynucleosides for the Synthesis of DNA Fragments Simplifying Deprotection and Isolation of the Final Product", Nucleic Acids Research, vol. 12, No. 11, pp. 4539-4557, (1984).

Stirchak, E. P. et al., "Uncharged Stereoregular Nucleic Acid Analogs: 2. Morpholino Nucleoside Oligomers with Carbamate Internucleoside Linkages", Nucleic Acids Research, vol. 17, No. 15, pp. 6129-6141, (1989).

Wenninger, D. et al., "Enzymatic and Hybridization Properties of Oligonucleotide Analogues Containing Novel Phosphotriester Internucleotide Linkage", Nucleosides & Nucleotides, vol. 17, No. 9-11, pp. 2117-2125, (1998).

Wilk, A. et al., "The 4-[N-Methyl-N-(2,2,2-trifluoroacetyl)amino]butyl Group as an Alternative to the 2-Cyanoethyl Group for Phosphate Protection in the Synthesis of Oligodeoxyribonucleotides", Journal of Organic Chemistry, vol. 64, No. 20, pp. 7515-7522, (1999).

Zalipsky, S., "Functionalized Poly(ethylene glycol) for Preparation of Biologically Relevant Conjugates", Bioconjugate Chemistry, vol. 6, pp. 150-165, (1995).

Sigmund et al., "Nucleotides A New Type of Labelling of Nucleosides and Nucleotides", Helvetica Chimica Acta., pp. 2299-2334, vol. 86, 2003.

Cao et al., "Molecular Beacon Aptamers for Protein Monitoring in Real-Time and in Homogeneous Solutions," *Current Proteomics*, vol. 2, pp. 31-40, 2005.

De Franciscis and Cerchia, "Nucleic Acid-Based Aptamers as Promising Therapeutics in Neoplastic Diseases," *Methods in Molecular Biology*, vol. 361, pp. 187-200, 2006.

Fang et al., "Molecular Beacons Novel Fluorescent Probes," *Analytical Chemistry*, vol. 72, Dec. 1, pp. 747A-753A, 2000.

Frutos et al., "Method for Detection of Single-Base Mismatches Using Bimolecular Beacons," *J. Am. Chem. Soc.*, vol. 124, No. 11, pp. 2396-2397, 2002.

Landegren et al., "Reading Bits of Genetic Information: Methods for Single-Nucleotide Polymorphism Analysis," *Genome Research*, vol. 8, pp. 769-777, 1998.

Parkhurst et al., "Simultaneous Binding and Bending of Promoter DNA by the TATA Binding Protein: Real Time Kinetic Measurements," *Biochemistry*, vol. 35, pp. 7459-7465, 1996.

Rajendran and Ellington, "In Vitro Selection of Molecular Beacons," *Nucleic Acids Research*, vol. 31, No. 19, pp. 5700-5713, 2003.

* cited by examiner

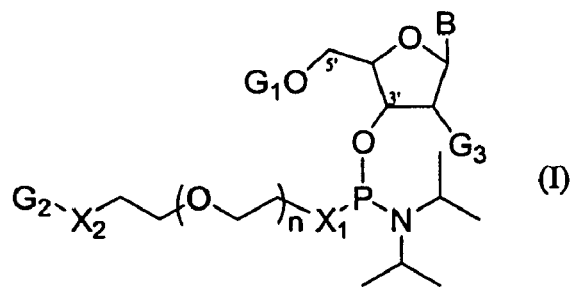
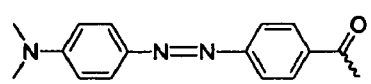
C1
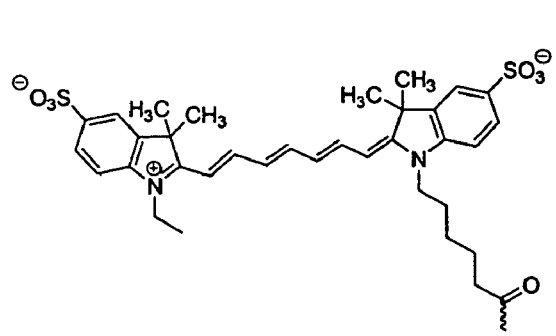
C2
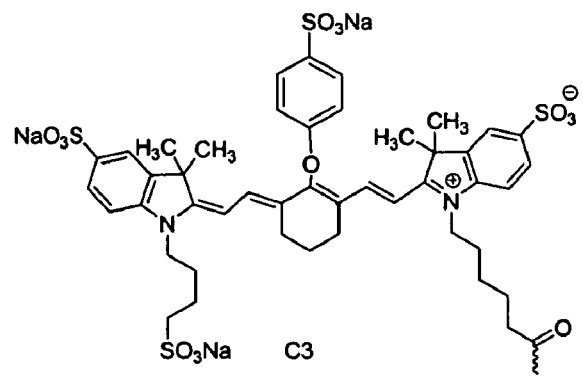
C3
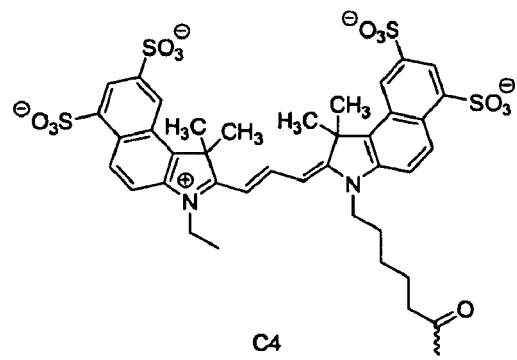
C4
FIG. 2

Cy3.5 NHS Ester

IRDye 800CW NHS Ester

Cy7 NHS Ester

13 dabcyl NHS Ester

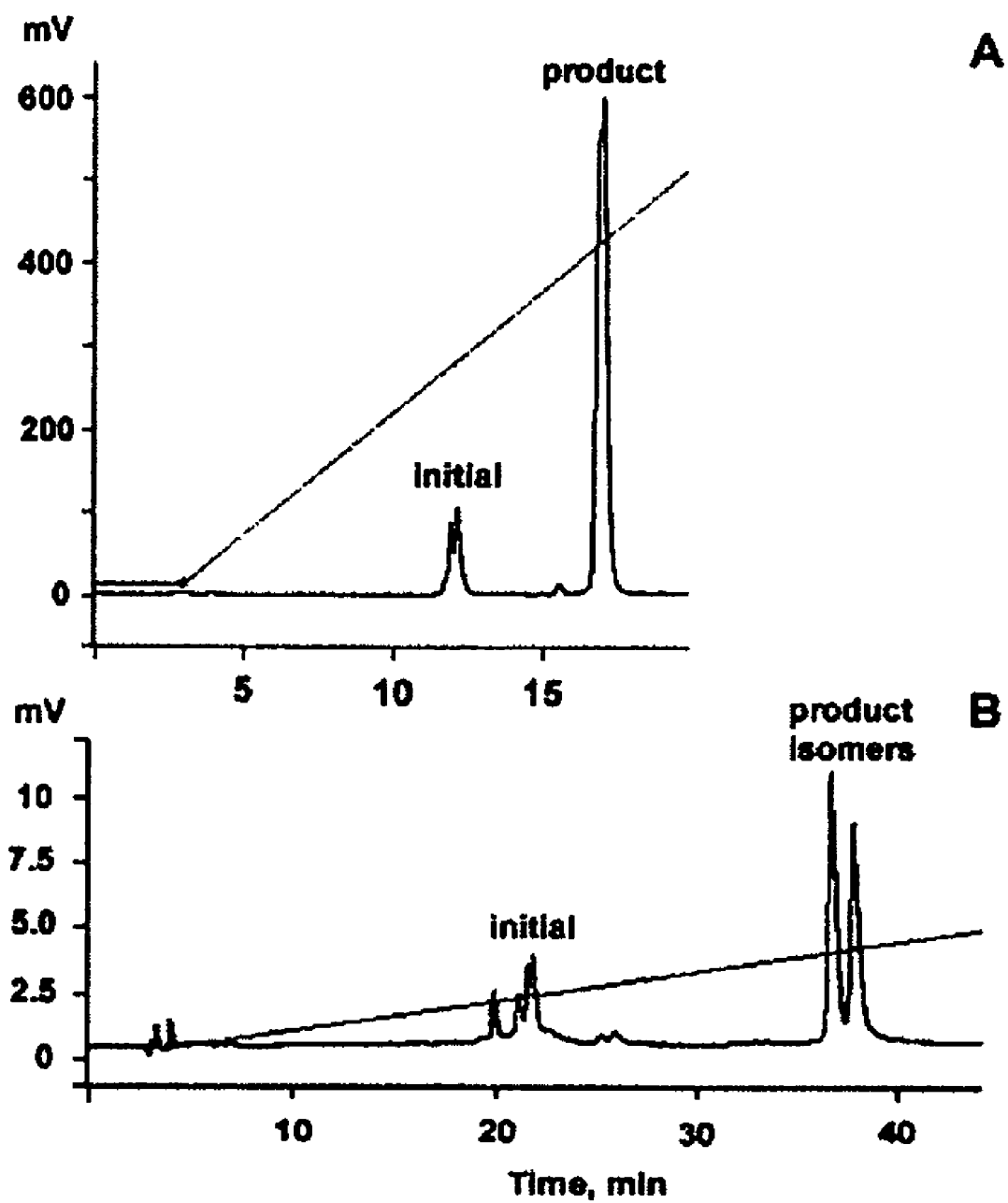
FIGS. 9A-B

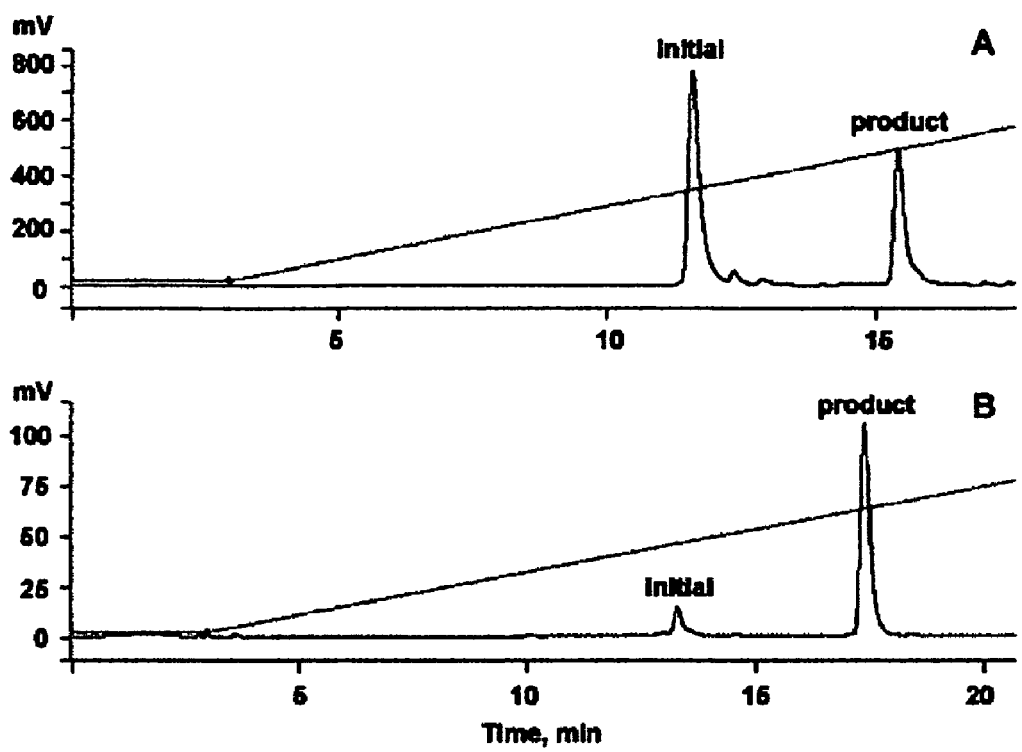
FIG. 10A-B
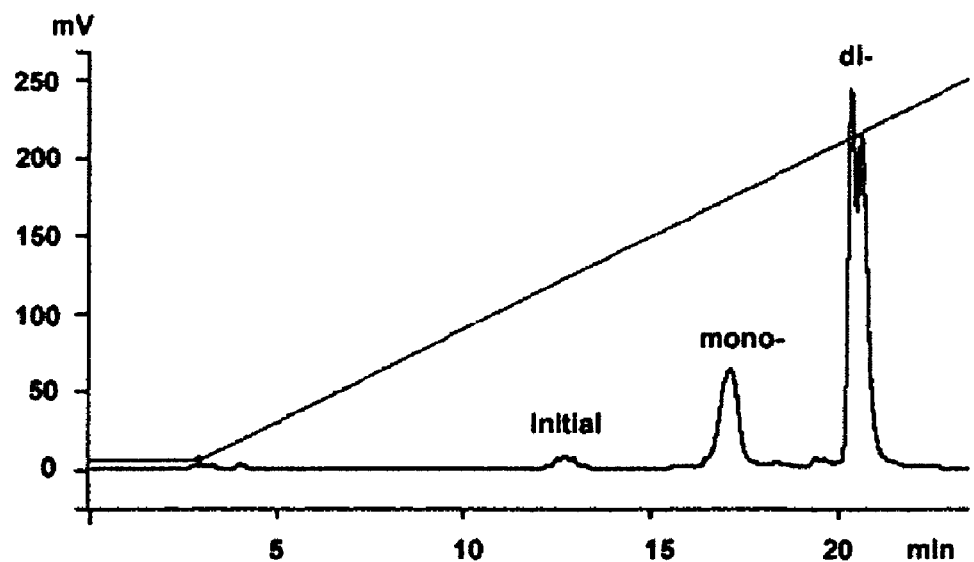
FIG. 11

FIG. 12A-B

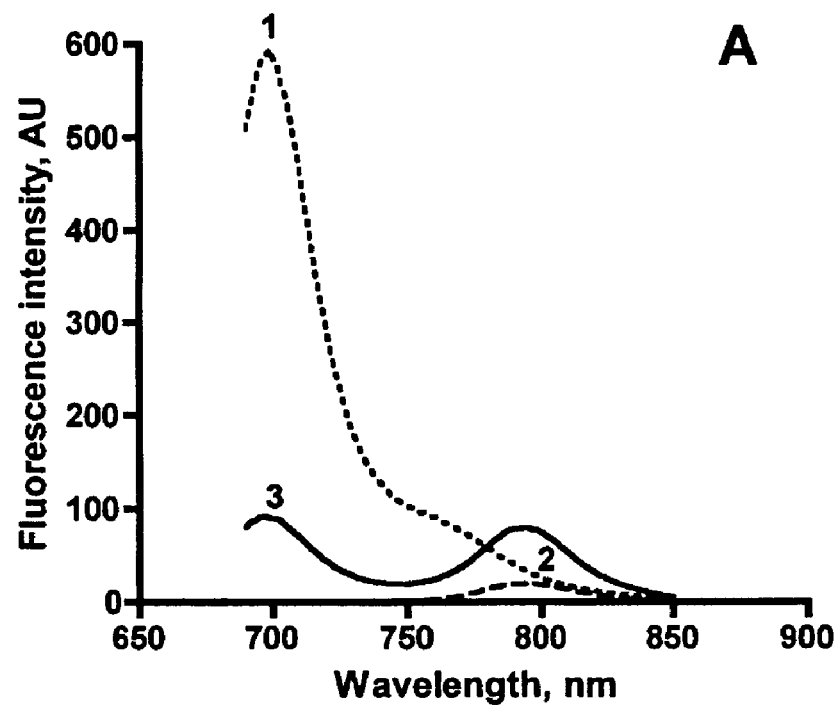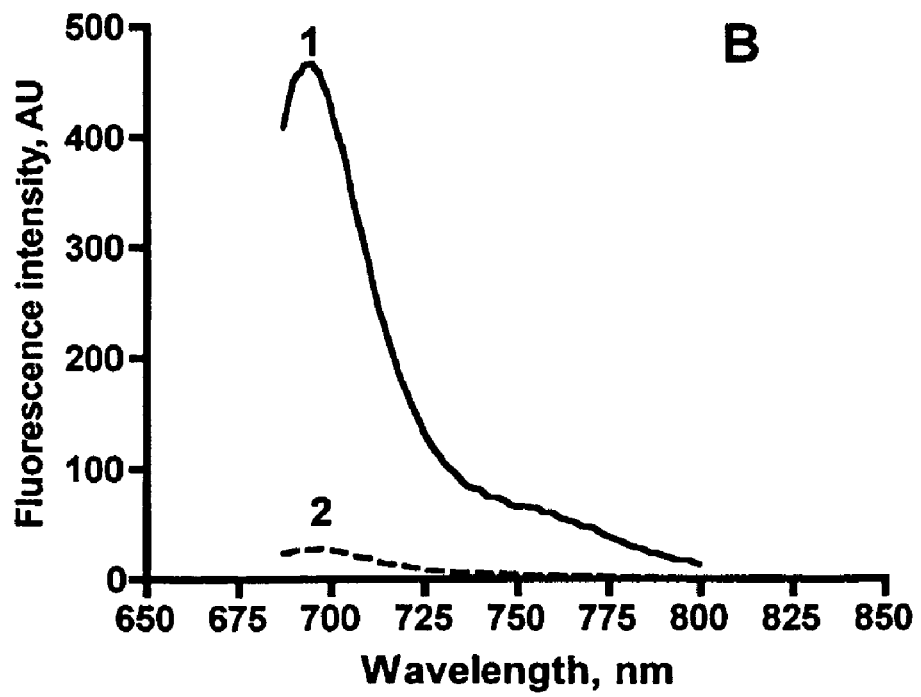
FIG. 14A-B

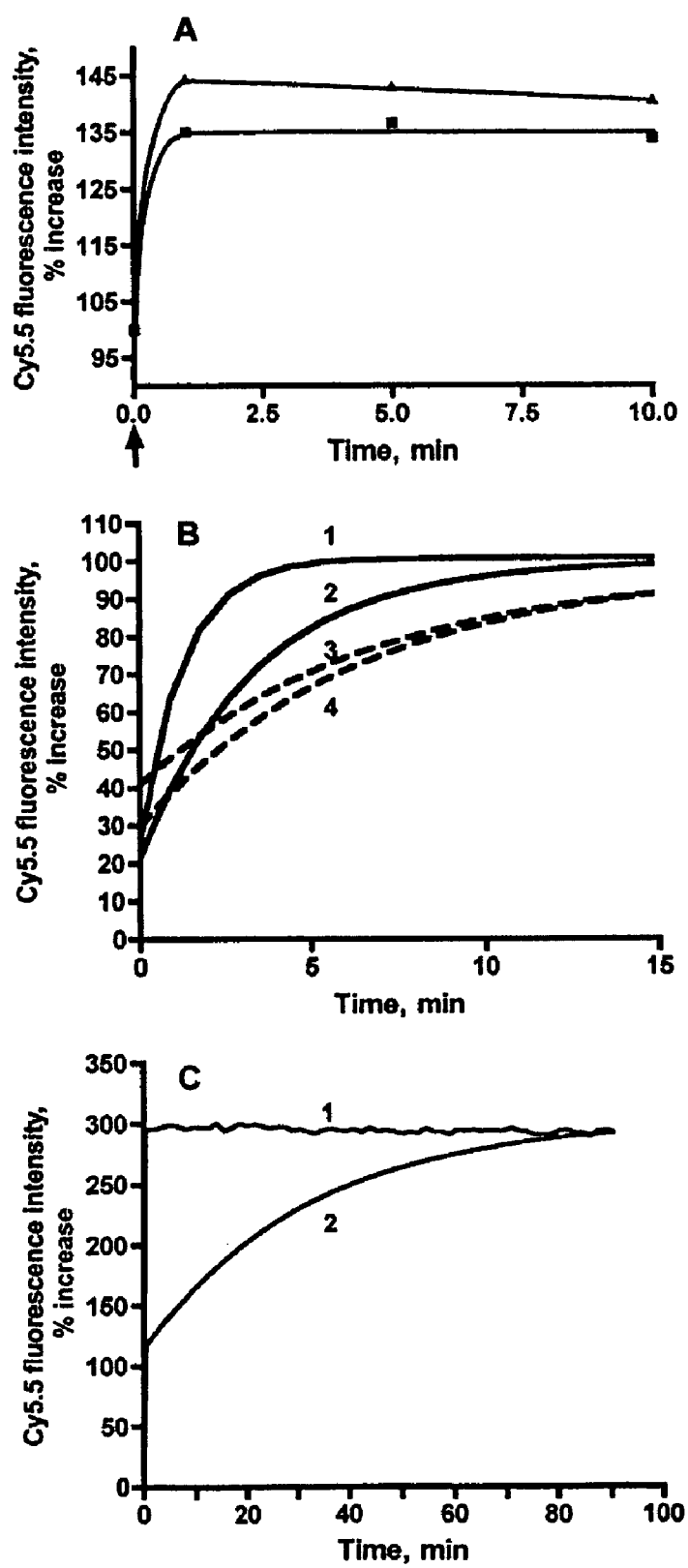
FIGS. 15A-C

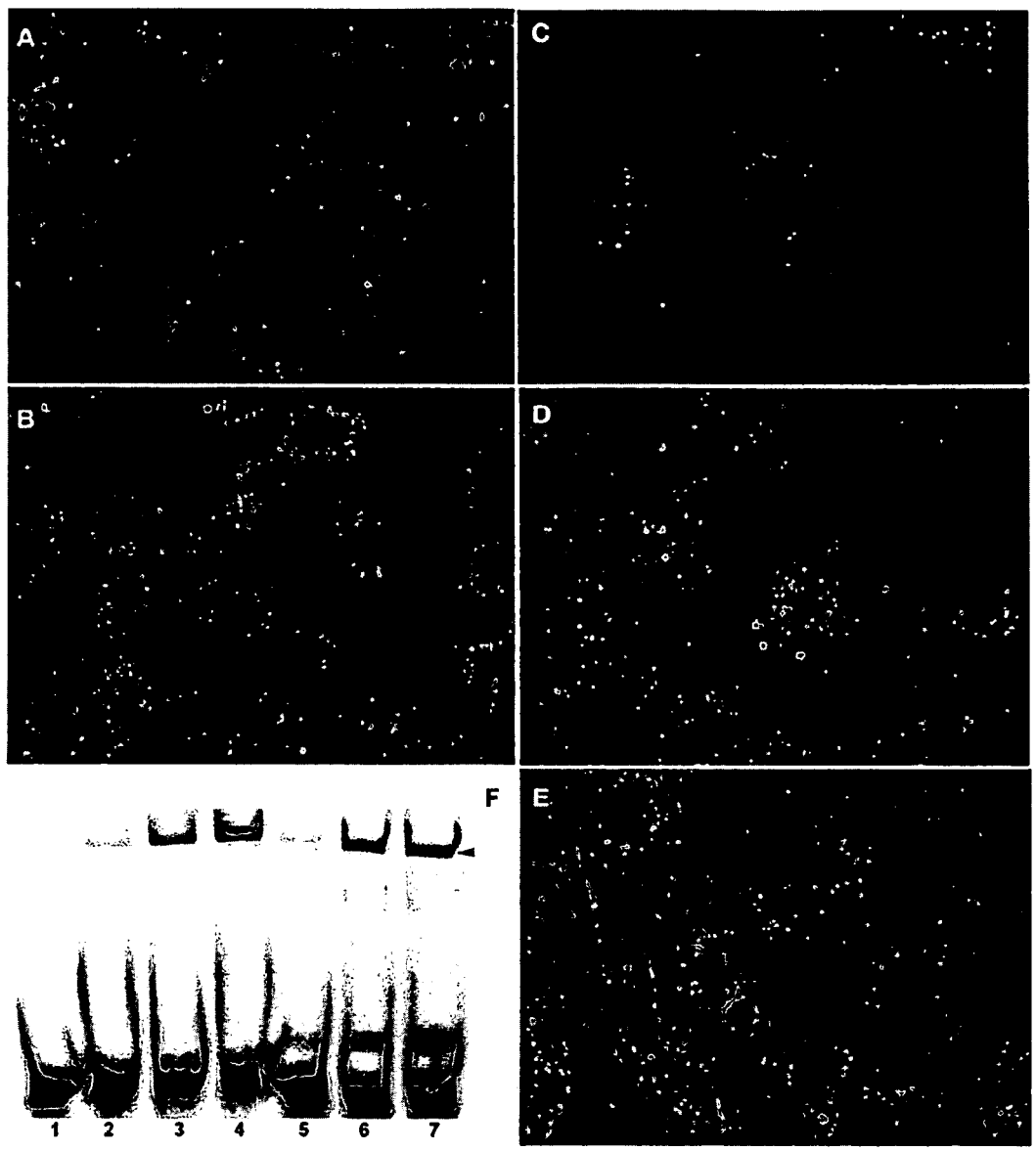
FIGS. 16A-F

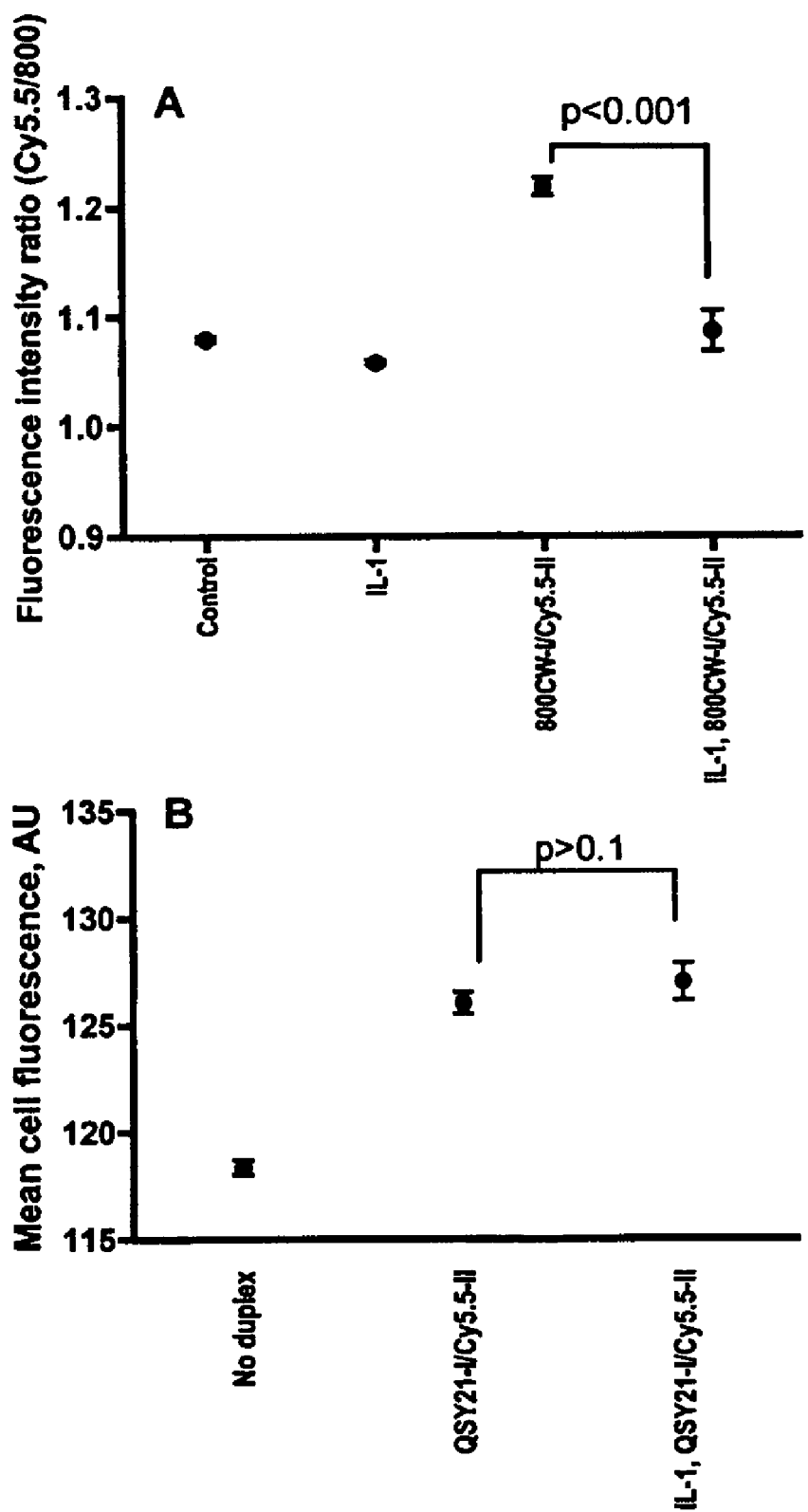
FIGS. 17A-B

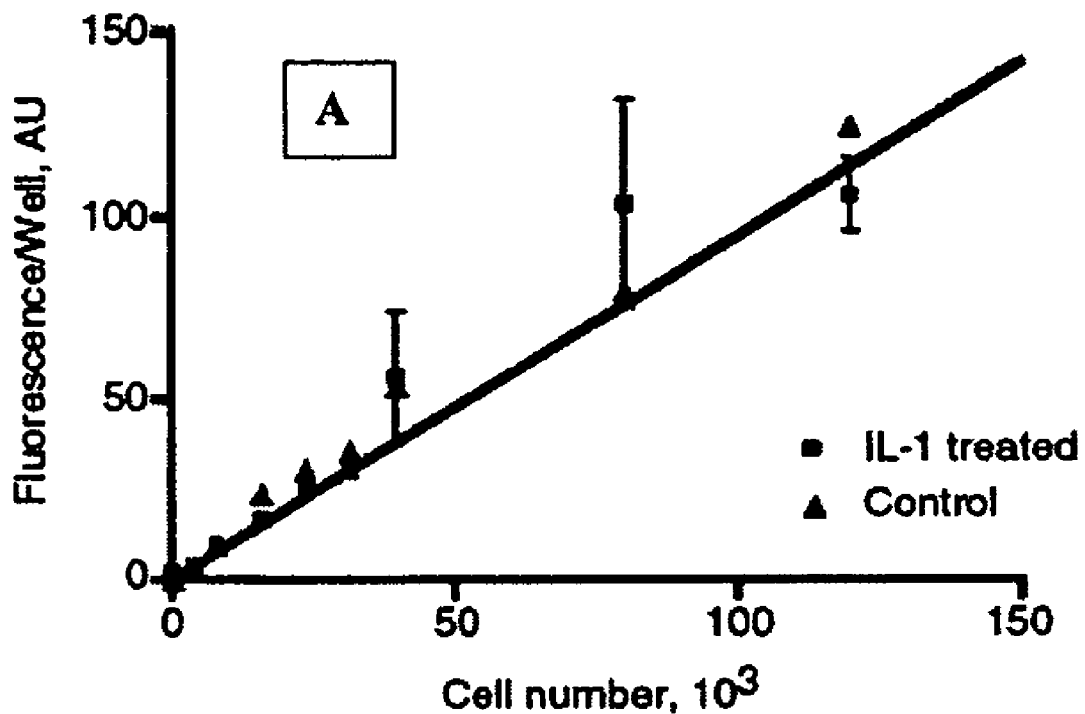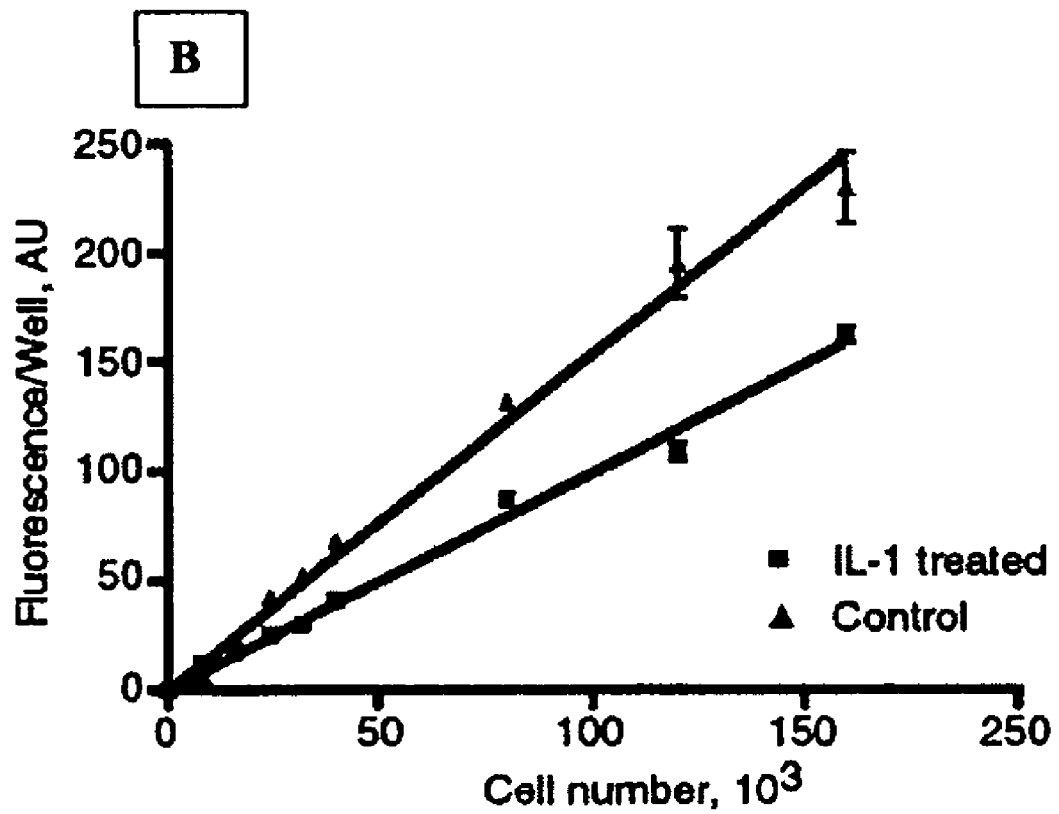
FIGS. 18A-B

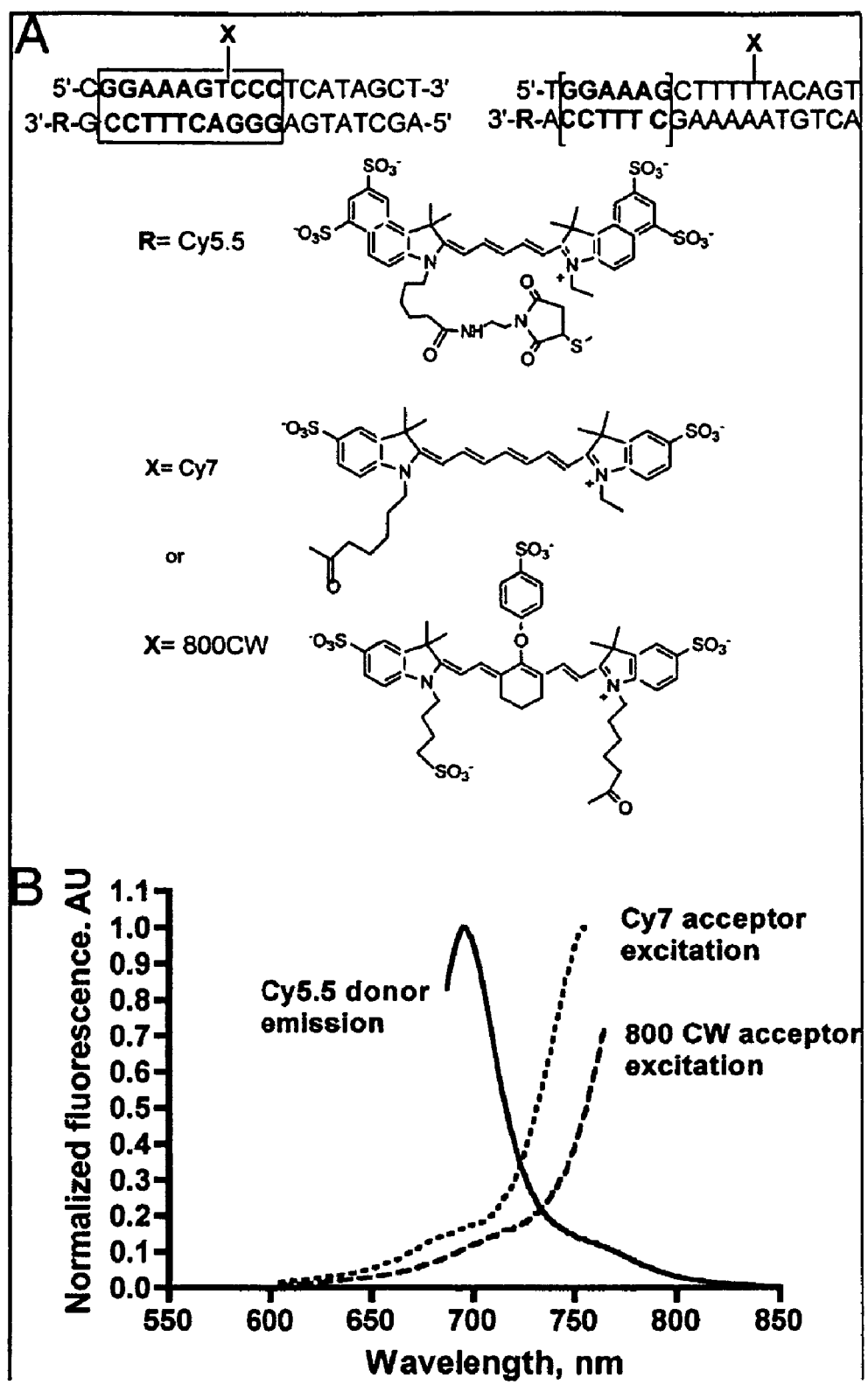
FIGS. 19A-B

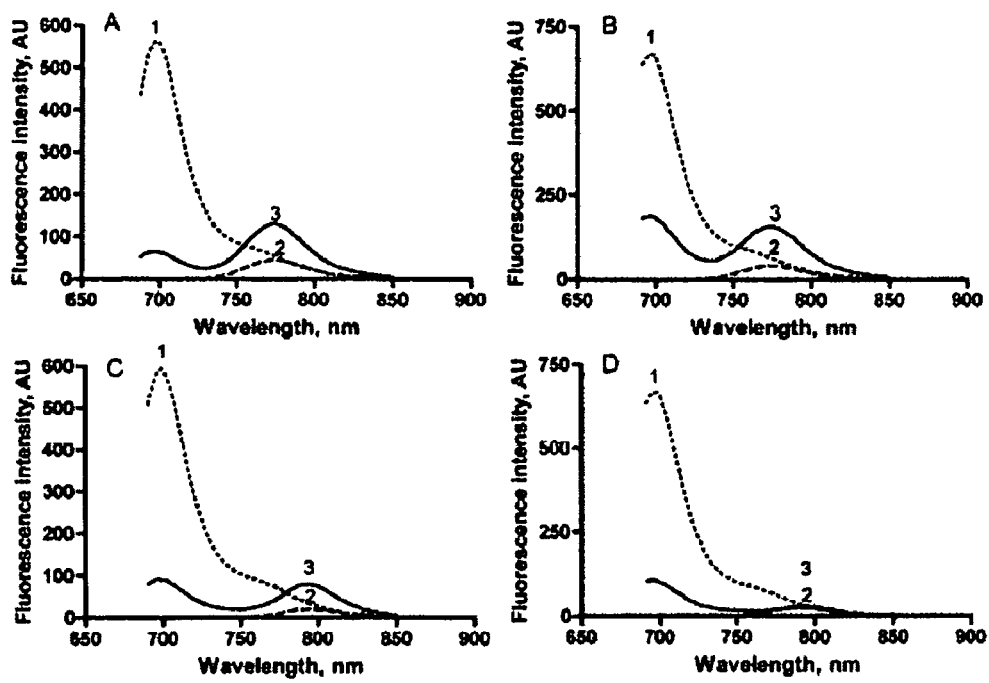
FIGS. 20A-D
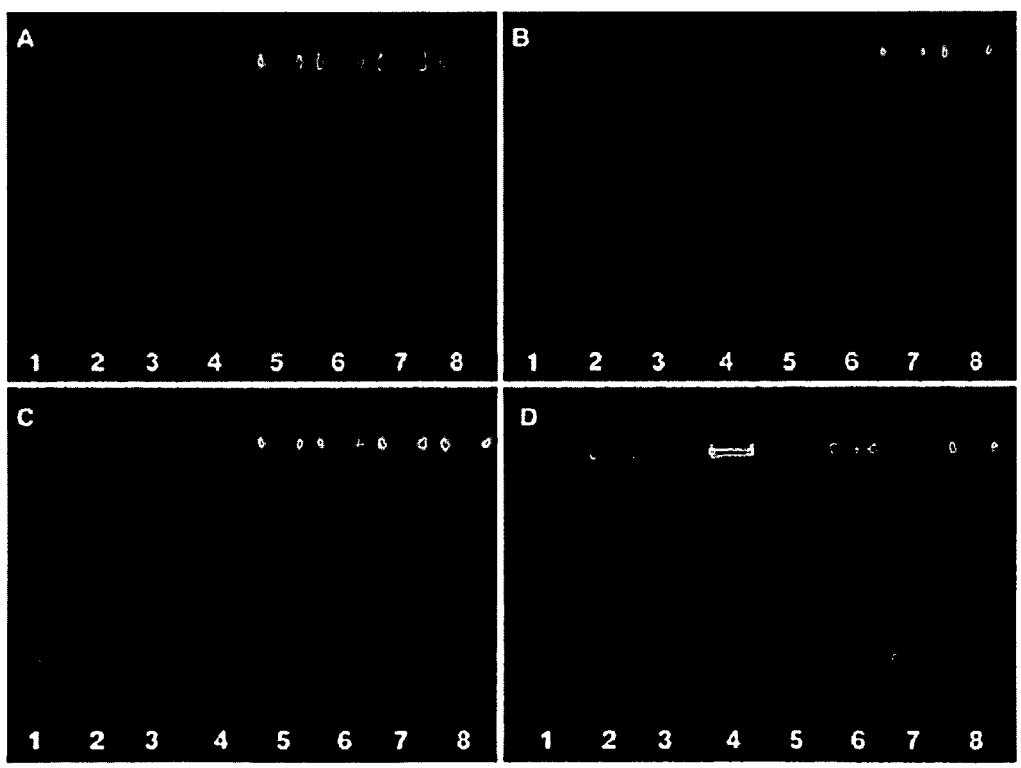
FIGS. 21A-D

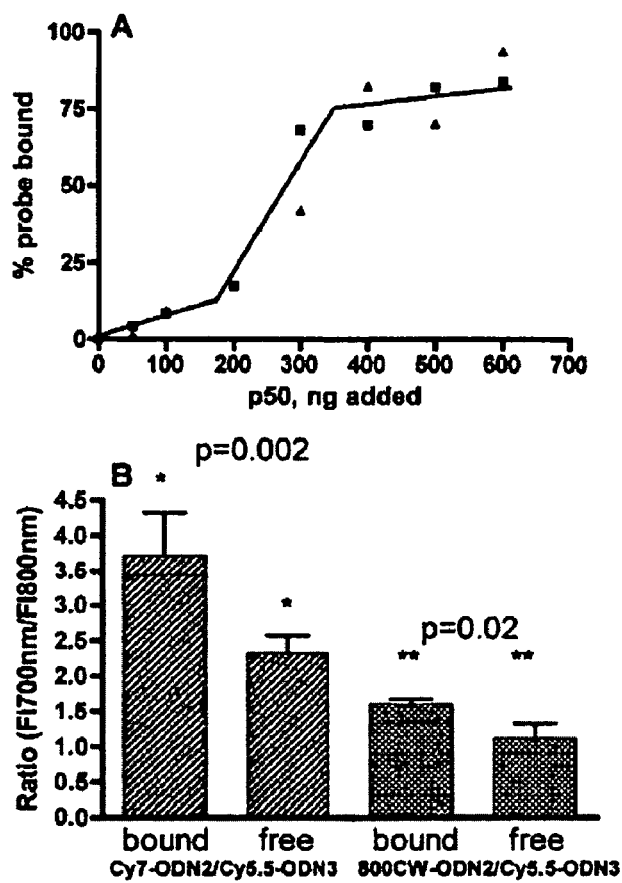
FIGS. 22A-B
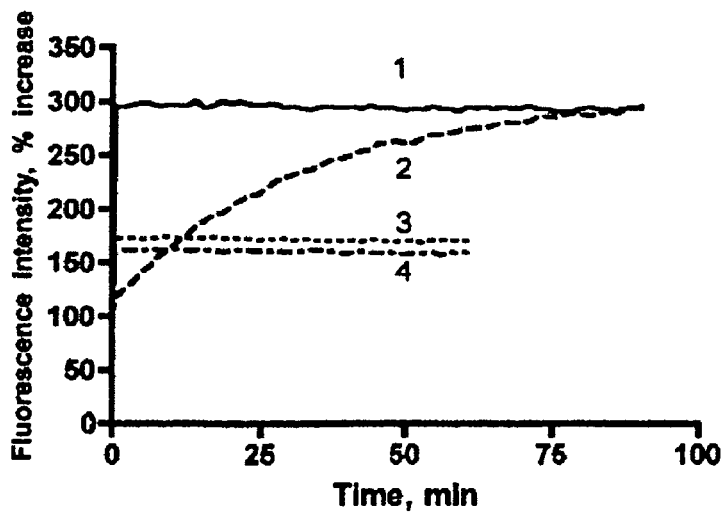
FIG. 23

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 1
cggaaagtcc ctcatagct                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 2
tggaaagctt tttacagtt                                              19

<210> SEQ ID NO 3
<211> LENGTH: 19
<212> TYPE: DNA
<213> ORGANISM: Artificial Sequence
<220> FEATURE:
<223> OTHER INFORMATION: Synthetically generated oligonucleotide

```
<400> SEQUENCE: 3
tggaaagctt tctatagtt                                                19

<210> SEQ ID NO 4
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 4
tggaaagctt tttatagtt                                                19

<210> SEQ ID NO 5
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 5
agctatgagg gactttccg                                                19

<210> SEQ ID NO 6
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20, 21
<223> OTHER INFORMATION: n = dT

<400> SEQUENCE: 6
cauuauaaau aucauucgcn n                                             21

<210> SEQ ID NO 7
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 7
aactgtaaaa agctttcca                                                19

<210> SEQ ID NO 8
<211> LENGTH: 10
<212> TYPE: DNA
<213> ORGANISM: Artificial Sequence
<220> FEATURE:
<223> OTHER INFORMATION: Synthetically generated oligonucleotide

<400> SEQUENCE: 8
ggaaagtccc                                                          10

<210> SEQ ID NO 9
<211> LENGTH: 7
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4
<223> OTHER INFORMATION: n = c or g
```

```
<220> FEATURE:
<221> NAME/KEY: misc_feature
<222> LOCATION: 6
<223> OTHER INFORMATION: n = c or a

<400> SEQUENCE: 9 tgantna                                                                    7

<210> SEQ ID NO 10
<211> LENGTH: 8
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 6
<223> OTHER INFORMATION: n = c or t
<220> FEATURE:
<221> NAME/KEY: misc_feature
<222> LOCATION: 7
<223> OTHER INFORMATION: n = c or a

<400> SEQUENCE: 10 tgacgnnr                                                                   8

<210> SEQ ID NO 11
<211> LENGTH: 13
<212> TYPE: DNA
<213> ORGANISM: Artificial Sequence
<220> FEATURE:
<223> OTHER INFORMATION: Synthetically generated oligonucleotide

<400> SEQUENCE: 11
gtgtcaaagg tca                                                            13

<210> SEQ ID NO 12
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 12 smggawgy                                                                   8

<210> SEQ ID NO 13
<211> LENGTH: 5
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = t or a

<400> SEQUENCE: 13 ngata                                                                      5

<210> SEQ ID NO 14
<211> LENGTH: 6
<212> TYPE: DNA
<213> ORGANISM: Artificial Sequence
<220> FEATURE:
<223> OTHER INFORMATION: Synthetically generated oligonucleotide
```

-continued

```
<400> SEQUENCE: 14 yaackg                                                                    6

<210> SEQ ID NO 15
<211> LENGTH: 8
<212> TYPE: DNA
<213> ORGANISM: Artificial Sequence
<220> FEATURE:
<223> OTHER INFORMATION: Synthetically generated oligonucleotide

<400> SEQUENCE: 15 caactgac                                                                  8

<210> SEQ ID NO 16
<211> LENGTH: 10
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 7
<223> OTHER INFORMATION: n = a, g, c or t

<400> SEQUENCE: 16 gggamtnycc                                                               10

<210> SEQ ID NO 17
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 17
acgtcatgac ct                                                            12

<210> SEQ ID NO 18
<211> LENGTH: 6
<212> TYPE: DNA
<213> ORGANISM: Artificial Sequence
<220> FEATURE:
<223> OTHER INFORMATION: Synthetically generated oligonucleotide

<400> SEQUENCE: 18 cacgtg                                                                    6
```

PHOSPHORAMIDITE NUCLEOSIDE ANALOGS

CROSS-REFERENCE TO RELATED APPLICATIONS

This application claims the benefit of U.S. Provisional Patent Application Ser. No. 60/967,184, filed on Aug. 31, 2007, which is incorporated herein by reference in its entirety.

FEDERALLY SPONSORED RESEARCH OR DEVELOPMENT

This invention was made with Government support under Grant Nos. R01 AI060872, awarded by the National Institute of Allergy and Infectious Diseases, R21 CA116144, awarded by the National Cancer Institute, and R01 EB000858, awarded by the National Institute of Biomedical Imaging and Bioengineering. The Government has certain rights in the invention.

TECHNICAL FIELD

This invention relates to nucleoside analogs, precursors thereof, oligonucleotides made from the analogs and conjugates of the oligonucleotides.

BACKGROUND

The use of synthetic phosphodiester oligonucleotides in living cells faces two major challenges: 1) rapid degradation of the compounds in vivo and 2) low uptake and inefficient transport through plasma membranes. To overcome these problems, various approaches have been tested in recent decades. One of the successful strategies has been synthesis of chemically modified oligonucleotides, particularly chemical modification of the backbones of oligonucleotides, insofar as this approach provides preservation of Watson-Crick hybridization properties of compounds. Synthetic oligonucleotides with phosphorothioate (Padmapriya et al., (1994) Antisense Res. Dev., 4, 185-199), methylphosphonate (Reddy et al., (1996) Tetrahedron Lett., 37, 8691-8694), boronophosphate (Shaw et al., (1993) Methods Mol. Biol., 20, 225-243), benzylphosphonate (Samstag et al., (1996) Antisense Nucleic Acids Drug Dev., 6, 153-156) modifications, locked nucleic acid (Kurreck et al., (2002) Nucleic Acids Res., 30, 1911-1918; Crinelli et al., (2002) Nucleic Acids Res., 30, 2435-2443), peptide nucleic acid (Egholm et al., (1993) Nature, 365, 566-568), morpholino derivatives (Stirchak et al., (1989) Nucleic Acids Res., 17, 6129-6141; Sinha et al., (1984) Nucleic Acids Res., 12, 4539-4557), and oligonucleotides with modified terminal groups (Shchepinov et al., (1997) Nucleic Acids Res., 25, 4447-4454; Shchepinov et al., (1999) Nucleic Acids Res., 27, 3035-3041; Horn et al., (1997) Nucleic Acids Res., 25, 4842-4849; Guzaev et al., (1995) Tetrahedron, 51, 9375-9384) have been widely tested as novel therapeutic agents (Monteith et al., (1999) Toxicol. Pathol., 27, 8-13; Ma et al., (2000) Biotechnol. Ann. Rev., 5, 155-196; Wilson and Richardson, (2006) Infect. Disord. Drug Targets, 6, 43-56) and diagnostic tools (Landegren et al., (1988) Science, 242, 229-237).

For some applications, native or modified synthetic oligonucleotides have to be linked to non-nucleotide molecules or surfaces. The non-nucleotide molecules could be fluorescent dyes or quenchers, metal chelators, ligands for various proteins, enzymes, receptors, transporters, or other biologically active molecules, hydrophobic residues, or even other oligonucleotides. The resultant conjugates may be useful as hybridization probes in DNA sequencing and microarray technology, as diagnostic and therapeutic agents, electron and fluorescent microscopy probes, and have roles in crystallography, affinity chromatography, and in cell biology research (Goodchild et al., (1990) Bioconjugate Chem., 1; 165-187; DaRos et al., (2005) Curr. Med. Chem. 12, 71-88; Boutorine et al., (2000) Molecular Biology, 34, 804-813; Urban and Noe, (2003) Farmaco, 58, 243-258; Silverman and Kool, (2006) Chem. Rev., 106, 3775-3789). Because oligonucleotides, with the exception of phosphorothioates, lack appropriately reactive functional groups for conjugate synthesis, introduction of such groups is necessary.

One of the most convenient and widely used groups for conjugation purposes is the aliphatic amino group. It can be coupled selectively and under mild conditions with ligands (reporters) bearing carboxylic groups or their activated derivatives, sulfonyl chlorides, isocyanates and isothiocyanates, aldehydes and alkylating residues, or other electrophilic functionalities. The amino group is usually attached to the oligonucleotide by a linker (spacer). The nature and the length of the linker are important for the synthesis and the function of the conjugates. Short linkers can create spatial restrictions, which lower the reactivity of the amino group and interfere with the function of the ligand and the oligonucleotide. Hydrophobic linkers, even when of sufficient length, tend collapse in aqueous environments, assuming globular conformations and again creating spatial crowding.

The site of the spacer attachment is another important factor in determining the properties of the conjugates. Traditionally, the spacer is attached at the 5'-end of the oligonucleotide upon the completion of the automated synthesis (Tang and Agrawal, (1990) Nucleic Acids Res., 18, 6461; Agrawal and Zamecnik, (1990) Nucleic Acids Res., 18, 5419-5423; Agrawal et al., (1986) Nucleic Acids Res., 14, 6227-6245; Kachalova et al., (2002) Helv. Chim. Acta., 85, 2409-2417). The attachment to the 3'-end on non-standard supports has also been explored (Markiewicz et al., (1997) Nucl. Acids Res., 25, 3672-3680). One drawback of both methods is that they do not allow position-specific modifications. If multiple reporters are to be attached, they cluster at the end of the oligonucleotide with no convenient strategy to vary their relative positions. When a reporter is to be placed within a certain sequence, or when multiple reporters are to be placed within a desired distance, intrastrand modification is necessary. The standard approach is to attach a linker to C-5 of the pyrimidine bases or C-8 of the purines. Deoxyribonucleoside phosphoramidites of this type with trifluoroacetyl-protected amino groups are commercially available. Thus, the design of the spacer and the place of its attachment in those synthons are driven more by consideration of synthetic convenience than by functionality. In the case of purines, an aliphatic spacer is attached to C-8 through an amino group, and in the case of pyrimidines, a carbamoylvinyl group introduced at C-5 is in conjugation with the base. Both alternatives could potentially result in interfering with normal base pairing.

The attachment of a linker to the internucleoside phosphates enables sequence-specific and multi-site labeling, minimally perturbs Watson-Crick base pairing and, importantly, provides stabilization of the oligonucleotides toward nucleases (Wenninger et al., (1998) Nucleos. Nucleot., 17: 2117-2125; Awad et al., (2004) Nucleosides, Nucleotides & Nucleic Acids, 23, 777-787). Two major types of internucleoside modifications have been described: 1) using a spacer linked to the sulphur of phosphorothioates, and 2) phosphoramidate nitrogen-linked spacers (Agrawal and Zamecnik, (1990) Nucleic Acids Res., 18, 5419-5423). The first type of linker is generally prepared by alkylation of phosphorothioates, and the second by oxidation of H-phosphonates in the presence of 1,ω-diamines. Drawbacks of these strategies include incompatibility with the commonly used phosphoramidite-based automated oligonucleotide synthesis, and they may require additional post-synthetic modifications.

The attachment of a linker to the oxygen of the internucleoside phosphates has been explored using a sequence-specific attachment of 2-aminoethyl groups (Seliger et al., (1991) Nucleos. Nucleot. 10, 303-306). However, the short 2-3 carbon atom spacer is not optimal for further attachment of reporters or ligands to the amino group. Increasing the length of the spacer results in its destabilization, because of the intramolecular attack at the terminal amino group of carbon atom adjacent to the phosphate through a favorable five or six atom cyclic transition state, resulting in the spacer's scission. A 4-trifluoroacetamidobutyl group has been developed as an alternative to the cyanoethyl group for phosphate protection in oligonucleotide synthesis (Wilk et al., (1999) J. Org. Chem., 64, 7515-7522).

SUMMARY

The present invention is based, at least in part, on the development of phosphoramidite nucleoside analogs with hydrophilic linkers, allowing, e.g., incorporation of chemical groups with different compositions with hydrophilic linkers into oligonucleotides (also referred to herein as oligos) during automated synthesis, or attachment of the analogs or oligos comprising the linkers to a solid surface.

The methods and compositions described herein generally enable the incorporation of hydrophilic linkers on the internucleotide phosphate during synthesis, e.g., automated synthesis, of oligonucleotides, generally without the need of additional synthetic steps. The compositions also include conjugates of the internucleotide phosphate moieties of the oligonucleotide analogs with biochemically active groups, reporter groups, organic molecules, bio-molecules, small molecules or other chemical groups through the hydrophilic linker at the internucleoside phosphotriesters.

In one aspect, the invention features compounds of Structure (I), which is shown below:

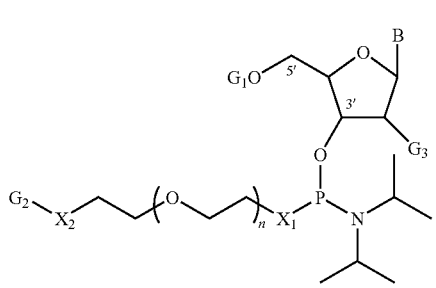
(I)

where, $G_1$ is H or a hydroxyl protecting group; B is a purine base residue, a pyrimidine base residue, a protected form of either base residue, or an analog of any of these; $X_1$ is S or O; n is an integer between 1 and 30, inclusive; $X_2$ is O, S or NH; $G_2$ is H, a protecting group or a moiety that includes a tag, a fluorochrome, a peptide, a polyethylene glycol moiety, or a quenching agent; and $G_3$ is a non-nucleophile and can be selected from the group of hydrogen, halogens, alkyl, alkoxy, alkoxyethoxy, or t-butyldimethylsilyloxy groups.

In another aspect, the invention features oligonucleotides that include an oligonucleotide sugar-phosphate backbone; a plurality of spaced apart bases, each bonded to a sugar unit of the sugar-phosphate backbone wherein the sugar unit is selected from a ribose sugar, a deoxyribose sugar or an analog thereof; and a linker moiety bonded to a phosphorus atom of the sugar-phosphate backbone and each moiety comprising Structure (II), which is shown below.

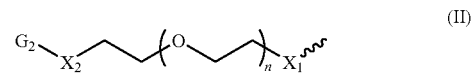
(II)

where, $X_1$ is S or O; n is an integer between 1 and 30, inclusive; $X_2$ is O, S or NH; and $G_2$ is H, a protecting group or a moiety that includes a tag, a fluorochrome, a peptide, a polyethylene glycol moiety, or a quenching agent.

In some embodiments, the invention features oligonucleotides including 50% or more, e.g., 60%, 70%, 75%, 80%, 85%, 90%, 95%, or 100% of the phosphorus atoms of the sugar-phosphate backbone are bonded to a linker moiety.

In another aspect, the invention features precursors to compounds of Structure (I) having Structure (III), which is shown below.

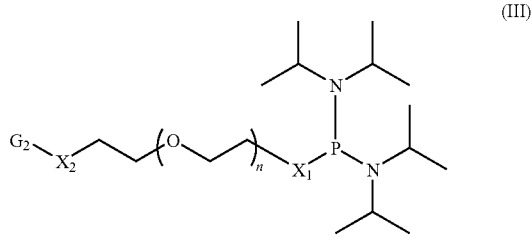
(III)

In such compounds, $X_1$ is S or O; n is an integer between 1 and 30, inclusive; $X_2$ is O, S or NH; and $G_2$ is H, a protecting group or a moiety that includes a tag, a fluorochrome, a peptide, a polyethylene glycol moiety, or a quenching agent.

In particular embodiments, the compounds of Structure (III) are represented by Structure (IV), which is shown below.

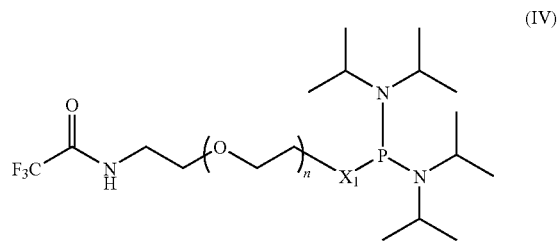
(IV)

In such instances, n can be, e.g., 1, 2, 3, 4, or 5; and $X_1$ can be O.

In another aspect, the invention features methods of making an oligonucleotide having a linker moiety. The method includes selecting an oligonucleotide that includes an oligonucleotide sugar-phosphate backbone having a plurality of spaced apart bases, each bonded to a sugar unit of the sugar-phosphate backbone, the sugar unit including a free hydroxyl group at the 5' position; and reacting a compound of Structure (I) with the selected oligonucleotide in a manner that the phosphorous atom of Structure (I) is bonded to the 5' oxygen atom of the oligonucleotide sugar-phosphate backbone to provide an oligonucleotide having a linker moiety. The compound of Structure (I) being:

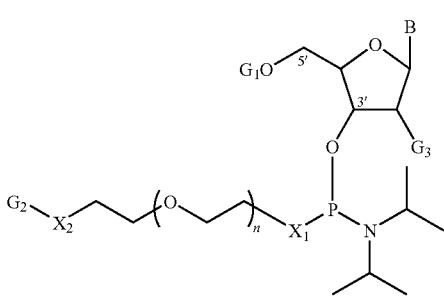

(I)

In such an aspect, $G_1$ is H or a hydroxyl protecting group; B is a purine base residue, a pyrimidine base residue, a protected form of either base residue, or an analog of any of these; $X_1$ is S or O; n is an integer between 1 and 30, inclusive; $X_2$ is O, S or NH; $G_2$ is H, a protecting group or a moiety that includes a tag, a fluorochrome, a peptide, a polyethylene glycol moiety, or a quenching agent; and $G_3$ is a non-nucleophile and can be selected from the group of hydrogen, halogens, alkyl, alkoxy, alkoxyethoxy, or t-butyldimethylsilyloxy groups.

In another aspect, the invention features methods of delivering an oligonucleotide into a cell. The method includes incubating the oligonucleotide with the cell, the oligonucleotide including an oligonucleotide sugar-phosphate backbone; and a linker moiety bonded to a phosphorus atom of the sugar-phosphate backbone, the linker moiety having the structure:

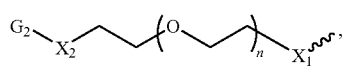

(II)

wherein, $X_1$ is S or O; n is an integer between 1 and 30, inclusive; $X_2$ is O, S or NH; and $G_2$ is H, a protecting group or a moiety that includes a tag, a fluorochrome, a peptide, a polyethylene glycol moiety, or a quenching agent.

In some embodiments, $G_2$ is a fluorochrome.

In some embodiments, $G_2$ is a quenching agent.

In some embodiments, $X_1$ is O; $X_2$ is NH; and $G_2$ is a fluorochrome.

In some embodiments, the oligonucleotide is a duplex oligonucleotide.

In some embodiments, the cell is an endothelial cell.

In some embodiments, the invention features oligonucleotides including 5% or more, e.g., 10%, 15%, 20%, 25%, or 50% or more of the phosphorus atoms of the sugar-phosphate backbone are bonded to a linker moiety.

In another aspect, the invention features methods of detecting a duplex oligonucleotide-protein interaction. The method includes contacting a protein with a duplex of. The oligonucleotide including a fluorochrome that can participate in fluorescence resonance energy transfer (FRET) (such as a linker of Structure (II)); measuring a fluorescence property of the oligonucleotide in the absence of the protein; measuring a fluorescence property of the oligonucleotide in the presence of the protein; and comparing the fluorescence property of the oligonucleotide in the absence of the protein with the fluorescence property of the oligonucleotide in the presence of the protein, wherein a difference in the fluorescence properties indicates an interaction between the duplex oligonucleotide and protein. In some embodiments, the detection can be performed in vitro or in the live cells.

The invention provides several advantages. For example, the nucleoside analogs described herein have superior cell permeability and stability, as compared to naturally occurring nucleosides. In addition, the nucleosides include linker moieties that can be used for attaching a number of compounds, including detectable reporter molecules, as well as for attaching oligos including the nucleoside analogs to a solid surface, e.g., a bead (such as a magnetic bead) or a glass or plastic surface (e.g., of an array or coverslip). The compositions and methods described herein also provide the ability to image specific DNA-protein interactions directly in intact living systems, greatly expanding the ability to directly characterize disease-specific transcriptional activation and downstream signal transduction events in vivo.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a generalized structure of phosphoramidite nucleoside analogs.

FIG. 2 shows a specific quenching moiety (C1) and a series of fluorochromes (C2-C4).

FIGS. 9A-B are line graphs showing the results of reverse phase HPLC analysis of reaction of amino-linker modified oligonucleotide I with dabcyl NHS ester leading to CGGAAAGT$^{dabcyl}$CCCTCATAGCT (X) (SEQ ID NO:3). Panel A, steep gradient. Panel B, shallow gradient. In the case of the shallow gradient the product is separated into two fractions, $X_1$ and $X_2$, due to the presence of two diastereomers, identical by mass spectrometry (Table 2).

FIGS. 10A-B are a pair of line graphs showing the results of reverse phase HPLC analysis of reaction mixtures of coupling of oligonucleotides with heptamethine cyanine IRDye 800CW. 10A, CGGAAAG^TCCCTCATAGCT (V) (SEQ ID NO:3). 10B, CGGAAAGT*CCCTCATAGCT (I) (SEQ ID NO:1).

FIG. 11 is a line graph showing the results of reverse phase HPLC analysis of the reaction mixture of coupling of TGGAAAGCTTTT*TAT*AGTT (IV) (SEQ ID NO:2) with dabcyl NHS ester. The presence of residual IV, the mono-adduct and the target product (TGGAAAGCTTTT$^{dabcyl}$-TAT$^{dabcyc}$AGTT, XVI) (SEQ ID NO:2) are shown.

FIG. 14A is a fluorescence spectra demonstrating FRET effect between Cy5.5-XIX donor ODN component (trace 1) and 800CW-I acceptor ODN (trace 2); 3-800CW-I/Cy5.5-XIX FRET effect.

FIG. 14B is a fluorescence spectra of I/Cy5.5-XIX (trace 1) and QSY21-I/Cy5.5-XIX probe (trace 2). Fluorescence was excited at 675 nm (Cy5.5 maximum).

FIGS. 15A-C are three line graphs. 15A, p50 destabilization of QSY21 quenching in QSY21-I/Cy5.5-XIX with the resultant dequenching of Cy5.5 fluorescence in QSY21-I/Cy5.5-XIX probe (1:1 ratio, triangles), in QSY21-I/Cy5.5-XIX probe (2:1 ratio, squares), p50 protein was added at t=0 minutes (arrow); 15B, p50 protection effect against Exo III degradation. 1—kinetics of dequenching in QSY21-I/Cy5.5-XIX probe (1:1 ratio) in the absence of p50; 2—kinetics of dequenching in QSY21-I/Cy5.5-XIX probe (2:1 ratio) in the absence of p50; 3—a delay in dequenching in the presence of p50 and QSY21-I/Cy5.5-XIX probe (1:1 ratio); 4—a delay in dequenching in the presence of p50 and QSY21-I/Cy5.5-XIX probe (2:1 ratio); 15C, 1—kinetics of FRET loss in 800CW-I/Cy5.5-XIX probe (1:1 ratio) in the absence of p50; 2—protective effect of p50 against Exo III degradation and resultant FRET loss in 800CW-I/Cy5.5-XIX probe (1:1 ratio).

FIGS. 16A-E are images of fluorescence microscopy of HUVEC. 16A, cells treated with IL-1 beta (2 pg/mL) and incubated with 800CW-I/Cy5.5-XIX probe (1 uM); 16B, no IL-1beta treatment, cells incubated with 800CW-I/Cy5.5-XIX probe (1 uM); 16C, control HUVEC; 16D, no IL-1beta treatment, cells incubated with 800CW-I/Cy5.5-XIX probe, stained with anti-E-selectin F(ab')2, and FITC-anti F(ab')2; 28E—treated with IL-1beta (2 pg/mL), incubated with 800CW-I/Cy5.5-XIX probe, stained with anti-E-selectin F(ab')2, and FITC-anti F(ab')2;

FIG. 16F is a image showing the results of an electrophoretic mobility shift assay (EMSA) of I/Cy5.5-XIX probe in the presence of HUVEC extracts. Lanes were as follows: 1) I/Cy5.5-XIX probe alone; 2) I/Cy5.5-XIX probe and nuclear extract (126 ng/μL) control, no treatment of HUVEC with IL-1beta; 3) I/Cy5.5-XIX probe and nuclear extract (126 ng/μL), cells treated with IL-1 beta; 4) nuclear extract (196 ng/μL); 5) I/Cy5.5-XIX probe and cytoplasmic extract (57 ng/μL) control, no treatment of HUVEC with IL-1beta; 6) I/Cy5.5-XIX probe and cytoplasmic extract (126 ng/μL), cells treated with IL-1beta; 7) same as 6), cytoplasmic extract (211 ng/μL); the arrowhead points to shifted probe bands.

FIGS. 17A-B are line graphs of fluorescence measurements in HUVEC culture. 17A, fluorescence intensity ratios (Cy5.5/800CW fluorescence) measured using microscopy of HUVEC cells that were non-treated, treated with IL-1beta in the absence of 800CW-I/Cy5.5-XIX probe or incubated with 800CW-I/Cy5.5-XIX in the absence or the presence of IL-1beta. 17B, measurements of Cy5.5 dequenching in HUVEC in the absence of IL-1 beta treatment and after the treatment, in the presence of QSY2—I/Cy5.5-XIX probe. The results are presented as mean±SD. Statistical significance was determined in groups of 20-30 cells/sample (2 independent experiments).

FIGS. 18A-B are fluorescence measurements in HUVEC culture; A: comparative uptake of non-FRET (I/Cy5.5-XIX) duplex probe. Note that there was no difference in the uptake in IL-1β treated (squares) or in control cells (triangles); B: Cy5.5 fluorescence in cells incubated in the presence of 800CW-I/Cy5.5-XIX FRET probe.

FIGS. 19A-B are illustrations of probe sequences, fluorochromes, and their spectral properties. 19A, structures of ODN duplex FRET NF-κB probes with the full-length GGAAAGTCCC (SEQ ID NO: 8) and truncated GGAAAG binding sites. FRET effect was achieved using Cy5.5 (R) as a donor of fluorescence, and Cy7 or 800CW (X) as acceptors. 19B, line graph showing spectral overlap between Cy5.5 donor emission (solid line) and Cy7 acceptor excitation (dotted line) or 800CW acceptor excitation (dashed line).

FIGS. 20A-D are line graphs showing the fluorescence spectra of ODN duplexes measured using λ=675 nm for excitation of Cy5.5 fluorescence: A—1-ODN3/Cy5.5-ODN3; 2—Cy7-ODN2/ODN3; 3—Cy7-ODN2/Cy5.5-ODN3; B—1-ODN3/Cy5.5-ODN3; 2—800CW-ODN2/ODN3; 3—800CW-ODN2/Cy5.5-ODN3; C—1-ODN4/Cy5.5-ODN5; 2—Cy7-ODN4/ODN5; 3—Cy7-ODN4/Cy5.5-ODN5; D-1-ODN4/Cy5.5-ODN5; 2—800CW-ODN4/ODN5; 3—800CW-ODN4/Cy5.5-ODN5.

FIGS. 21A-D are images of the results of two wavelength EMSA. 21A-C, concentration dependence of p50 binding to Cy7-ODN2/Cy5.5-ODN3: 21A, emission at 700 nm, 21B, emission at 800 nm; 21C, overlay (lane 1—0 ng p50, 2—50 ng, 3—100 ng, 4—200 ng, 5—300 ng, 6-400 ng, 7—500 ng, 8—600 ng). 21D, EMSA of p50 binding to two probe types. lane 1-ODN1/Cy5.5-ODN3; lane 2—300 ng p50+ODN1/Cy5.5-ODN3; lane 3—Cy7-ODN2/Cy5.5-ODN3; lane 4—300 ng p50+Cy7-ODN2/Cy5.5-ODN3; lane 5-ODN4/Cy5.5-ODN5; lane 6—300 ng p50+ODN4/Cy5.5-ODN5; lane 6-Cy7-ODN2/Cy5.5-ODN3; lane 7—300 ng p50+Cy7-ODN2/Cy5.5-ODN3.

FIGS. 22A-B are a line graph and a bar graph, respectively, illustrating the results of quantitative assessment of FRET. 22A, line graph of quantitation of concentration dependent EMSA shift of p50 binding to Cy7-ODN2/Cy5.5-ODN3 (emission at 700 nm) 22B, bar graph of ratiometric measurement of fluorescence intensities (700 nm and 800 nm) using free and p50-bound probes Cy7-ODN2/Cy5.5-ODN3 and 800CW-ODN2/Cy5.5-ODN3.

FIG. 23 is a line graph illustrating the effects of exonuclease III (1 U/sample) mediated hydrolysis on Cy5.5 donor fluorescence changes as measured in the absence (1, 3) and in the presence (2, 4) of p50 using Cy7-ODN2/Cy5.5-ODN3 (1,2) or Cy7-ODN4/Cy5.5-ODN5 (3, 4) probes.

DETAILED DESCRIPTION

Figure 3:
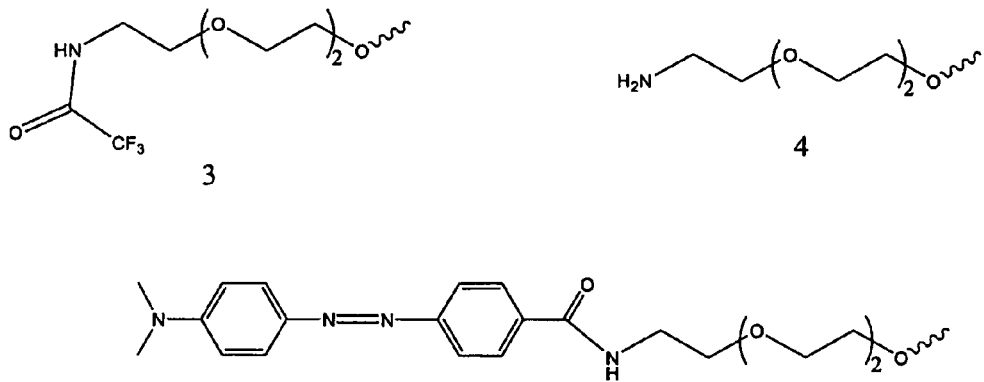
FIG. 3 shows specific structures for several specific linking moieties that can be tethered to an oligonucleotide.

Described herein are phosphoramidite nucleoside analogs, which can be used for incorporating nucleophiles, such as primary amino groups or thiol groups or protected nucleophiles, through a glycol spacer, such as a hydrophilic polyethylene glycol spacer, to the internucleoside phosphate at one or more desired locations. For example, ω-aminoalkyl (terminal) derivatives that are sufficiently stable under alkaline deblocking conditions for position-specific attachment of ligands or reporter groups, to the internucleoside phosphates, are described herein, as well as oligonucleotides including the analogs, and method of making and using the same.

Nucleoside Analogs, Oligonucleotides and Precursors

Referring to FIG. 1, nucleoside analogs of Structure (I) are provided in which $G_1$ is H or a hydroxyl protecting group; B is a purine base residue, a pyrimidine base residue, a protected form of either base residue, or an analog of any of these; $X_1$ is S or O; n is an integer between 1 and 30, inclusive; $X_2$ is O, S or NH; and $G_2$ is H, a protecting group or a moiety that includes a tag (such as biotin, digoxigenin), a chromophore, a fluorochrome, a peptide, a polyethylene glycol moiety, or a quenching agent (a reporter moiety); and $G_3$ is a non-nucleophile and can be selected from the group of hydrogen, halogens, alkyl, alkoxy, alkoxyethoxy, or groups.

When $G_1$ is a hydroxyl protecting group, $G_1O$ can define part of an alkyl ether (such as a methyl or ethyl ether), an aryl ether (such as a phenyl or dimethoxytrityl ether), an arylalkyl ether (such as a benzyl ether), a silyl ether (such as t-butyldimethylsilylether) or a carbonate (such as an aryl carbonate).

In specific implementations, $G_1$ is dimethoxytrityl (DMTr).

In some embodiments, B is one of B1 to B5 or a protected form of B1 to B5.

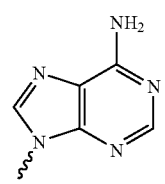

adenine residue

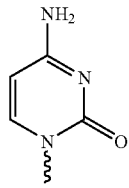

cytosine residue

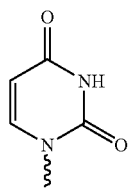

uracil residue

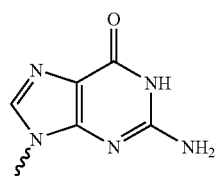

guanine residue

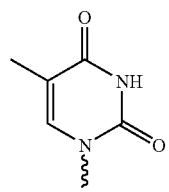

thymine residue

For example, the nucleophilic amino group of the guanine residue can be protected with a 4-isopropylphenoxyacetyl group, the nucleophilic amino group of the adenine residue can be protected with a phenoxyacetyl group and the nucleophilic amino group of the cytosine residue can be protected with an acetyl group.

B can also be, e.g., a minor base residue, such as pseudouridine residue, which connects to a sugar via a carbon-carbon bond instead of a carbon-nitrogen bond; a 7-methylguanine residue; a 5-methylcytosine residue; or a naturally occurring base residue analog.

In some embodiments, n of the hydrophilic glycol spacer is between 2 and 20, inclusive, e.g., 3, 4, 5, 6, 7, 8, 9, 10, 11, 12, 13, 14, 15, 16, 17, 18 or 19. In some embodiments, n is 1, 2, 3, or 4, between 2 and 6, inclusive, or between 2 and 10, inclusive. In some embodiments, n is less than about 15, e.g., less than about 10 or less than about 8.

In certain embodiments, $X_2$ is NH.
In certain embodiments, $X_2$ is NH and $G_2$ is $CF_3C(=O)$.
In certain embodiments, $G_2$ is H and $X_2$ is NH.
In certain specific embodiments, $G_1$ is DMTr, B is B5 (thymine residue), $X_1$ is O, n is 1, 2, 3, 4, or 5, $X_2$ is NE and $G_2$ is $CF_3C(=O)$. For example, compounds 1 and 2 (compound 2 being a protected form of compound 1) are structures for specific molecules of compounds of Structure (I).

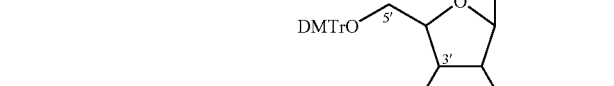
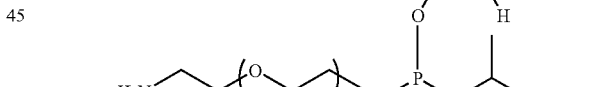
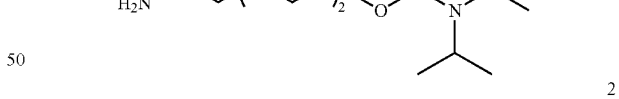
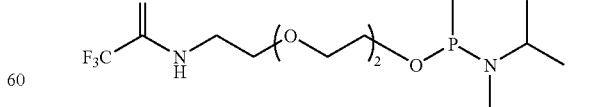

The nucleoside analogs of Structure (I) can be used to make oligonucleotides or functionalized oligonucleotides.

Generally, oligonucleotides that include an oligonucleotide sugar-phosphate backbone, a plurality of spaced apart bases, each bonded to a sugar unit of the sugar-phosphate backbone and one or more linker moieties, each bonded to a phosphorus atom of the sugar-phosphate backbone and each including a moiety of Structure (II) can be provided.

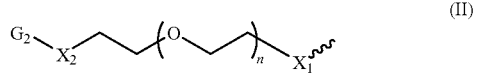

(II)

In such oligonucleotides, $X_1$ is S or O; n is an integer between 1 and 30, inclusive; $X_2$ is O, S or NH; and $G_2$ is H, a protecting group or a moiety that includes a tag, a fluorochrome, a peptide, a polyethylene glycol moiety, or a quenching agent.

In some embodiments, n of the hydrophilic glycol spacer is between 2 and 20, inclusive, e.g., 3, 4, 5, 6, 7, 8, 9, 10, 11, 12, 13, 14, 15, 16, 17, 18 or 19. In some embodiments, n is 1, 2, 3, or 4, between 2 and 6, inclusive or between 2 and 10, inclusive. In some embodiments, n is less than about 15, e.g., less than about 10 or less than about 8.

In certain embodiments, $X_2$ is NH and $G_2$ is $CF_3C(=O)$.

In certain embodiments, $G_2$ is H and $X_2$ is NH.

In certain embodiments, $X_2$ is NH and $G_2$ is the quenching moiety C1 of FIG. 2 of any one of the fluorochromes C2-C4 of FIG. 2.

Referring now to FIG. 3, in specific implementations, the moiety of Structure (II) is represented by specific structures 3, 4, or 5.

Figure 4:
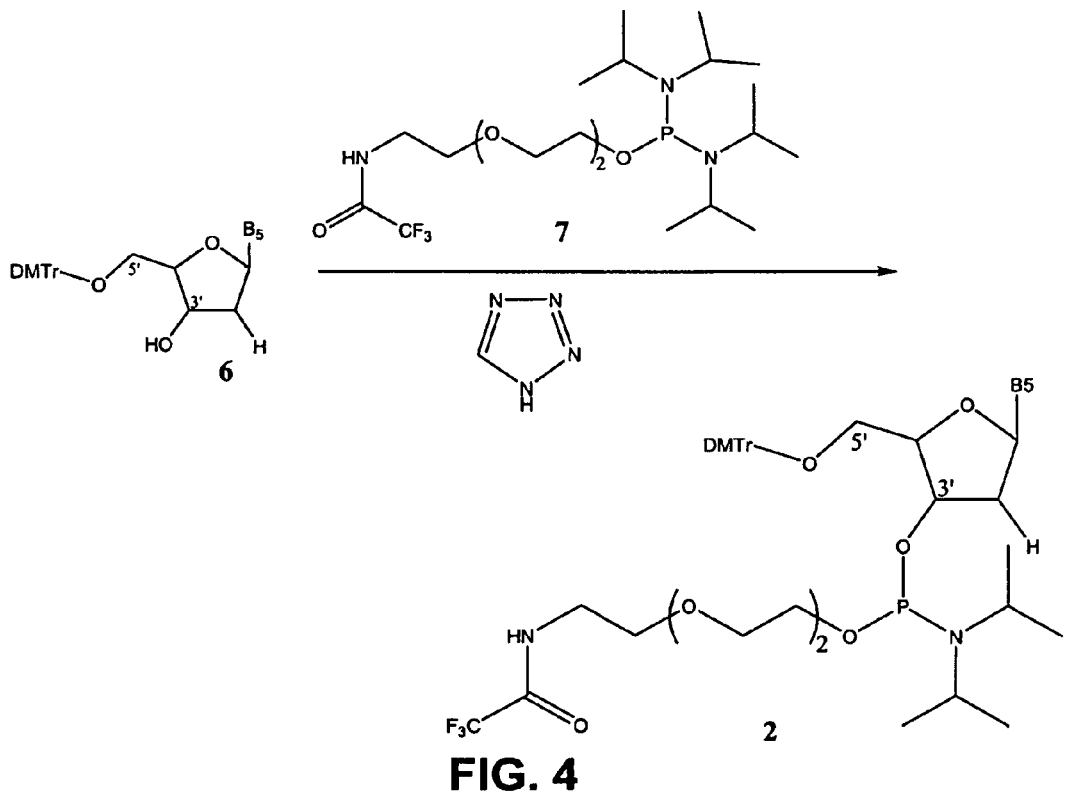
FIG. 4 shows a synthetic scheme for making a specific phosphoramidite nucleoside analog.

FIG. 4 shows that specific amino-protected nucleoside analog 2 can be prepared by reacting sugar 6 with protected phosphorus compound 7 in the presence of base. More generally, compound 7 can be replaced by compounds of Structures (III) or (IV).

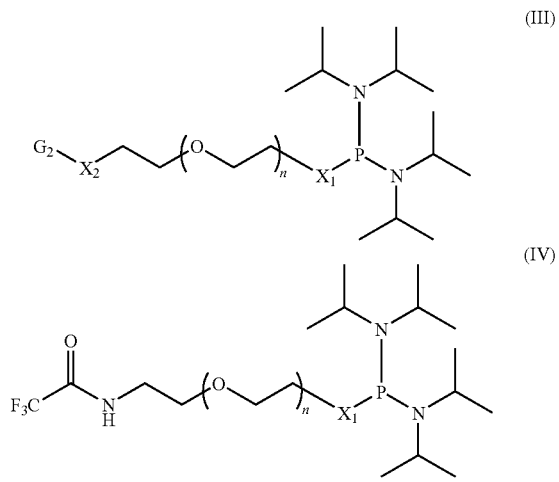

Embodiments of Structure (III) can have one or more of the following. n is an integer between 1 and 20, inclusive e.g., 2, 3, 4, 5, 6, 7, 8, 9, 10, 11, 12, 13, 14, 15, 16, 17, 18 or 19.

In certain embodiments, $G_2$ is $CF_3C(=O)$.

In certain embodiments, $G_2$ is $CF_3C(=O)$ and $X_2$ is NH.

Figure 5:
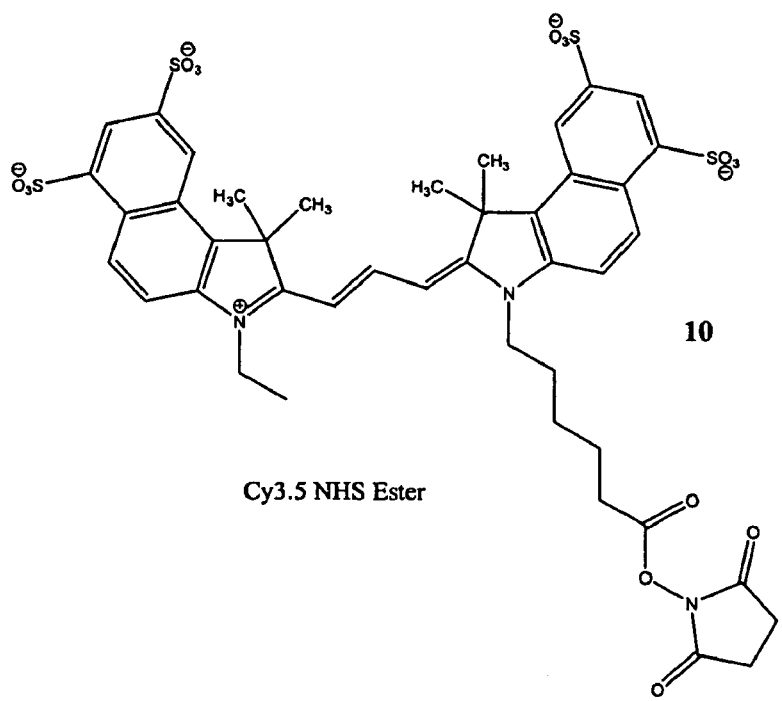
FIGS. 5-7 show a series of reactive NHS ester dyes that can be conjugated to oligonucleotides having a linker moiety that includes a nucleophilic group, such as an amino group or a thiol group.
Figure 6:
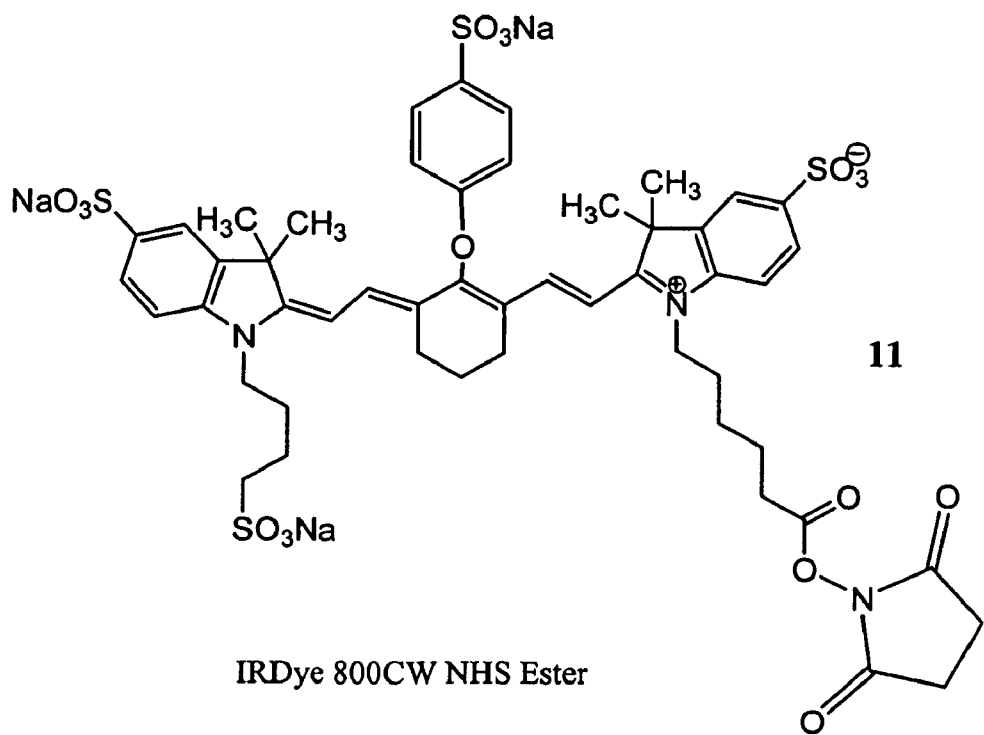
Figure 7:
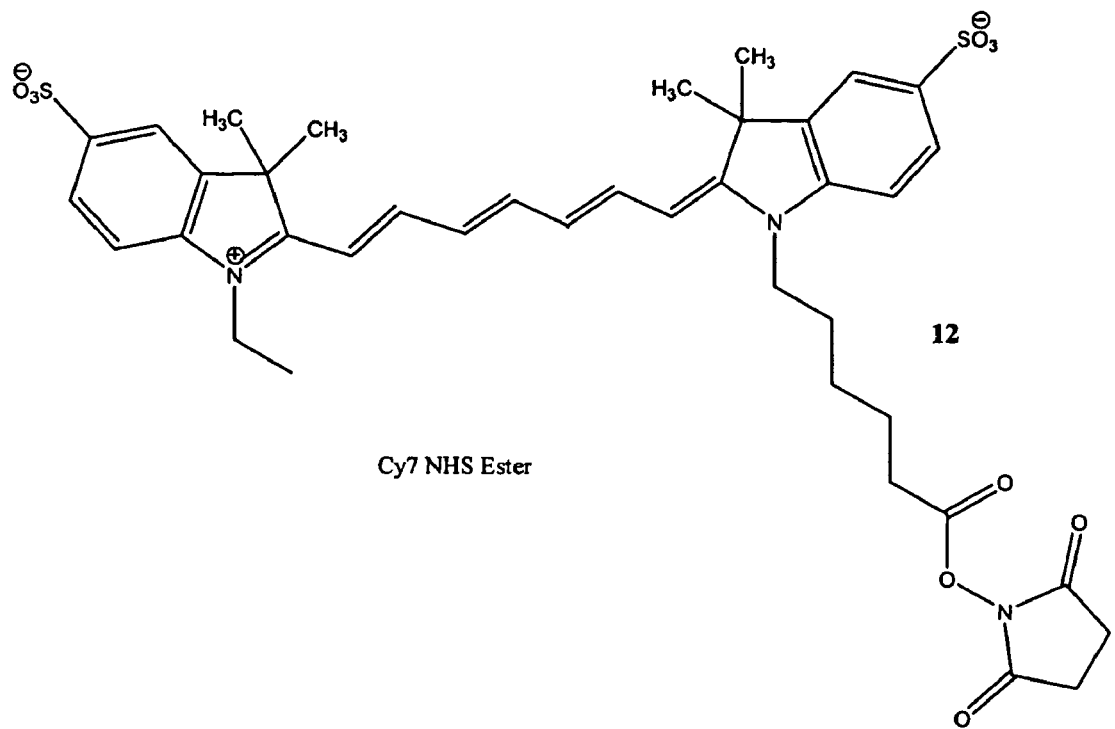
Figure 8:
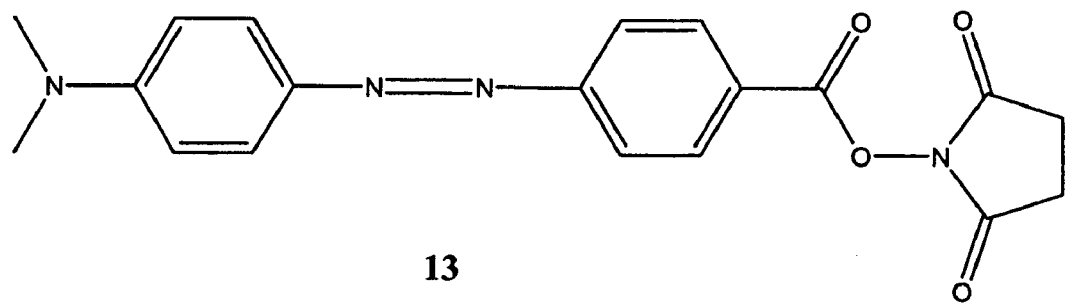
FIG. 8 shows a reactive NHS ester quenching agent that can be conjugated to oligonucleotides having a linker moiety that includes a nucleophilic group, such as an amino group or a thiol group.

Referring back now to Structure (II) and FIGS. 5-8, oligonucleotides having linkers of Structure (II) in which $G_2$-$X_2$ defines an amino group or a thiol group, can be reacted with the NHS-ester functionalized dyes of FIGS. 5-7 or the NHS-ester functionalized quenching agent of FIG. 8 to provide dye- or quenching agent-functionalized oligonucleotides, which are described in more detail below.

Referring back now to FIG. 1 and Structure (II) and as described in more detail below, oligonucleotides having one or more linker moieties represented by Structure (II) can be prepared by selecting an oligonucleotide that includes an oligonucleotide sugar-phosphate backbone having a plurality of spaced apart bases, each bonded to a sugar unit of the sugar-phosphate backbone; and reacting a compound of Structure (I) with the selected oligonucleotide in a manner that one or more linker moieties become bonded to one or more respective phosphorus atoms of the oligonucleotide sugar-phosphate backbone.

Specific Oligonucleotides

Within the scope of the present invention are oligonucleotides, also referred to herein as oligos, comprising two or more nucleotides, at least one of which is a nucleotide analog described herein. In some embodiments, the oligos can be DNA, i.e., include deoxyribonucleotides, or RNA, i.e., include ribonucleotides. The oligos can be single stranded or double stranded.

In some embodiments, an RNA oligo can be a small interfering RNA (siRNA), for use in RNA interference (RNAi). Synthons of ribo- or deoxyribonucleoside analogs of the invention can be incorporated into oligoribonucleic acids and their derivatives during automated synthesis according to protocols employed for solid phase synthesis of natural RNAs or their 2'-OMe, 2'-F modified RNA phosphoramidites [Usman et al., J. Am. Chem. Soc., 109: 7845-7854 (1987); Pitsch et al., Helv. Chim. Acta, 84: 3773-3795 (2001); Semenyuk et al., J. Am. Chem. Soc., 128: 12356-12357 (2006); Sproat et al., Nucleic Acids Res., 13: 2979-2987 (1985); Sproat et al., Nucleic Acids Res., 17: 3373-3386 (1989); Inoue et al., Nucleic Acids Symp Ser., 16:165-168 (1985); Prakash et al., Curr. Top. Med. Chem., 7:641-649 (2007)].

RNAi is a process whereby double-stranded RNA (dsRNA, also referred to herein as si RNAs or ds siRNAs, for double-stranded small interfering RNAs) induces the sequence-specific degradation of homologous mRNA in animals and plant cells (Hutvagner and Zamore, Curr. Opin. Genet. Dev. 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell. 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

In some embodiments, the oligos are antisense oligos, of about 6 to about 60 bases, preferably from about 9 to about 50 bases, more preferably from about 12 to about 25 bases, most preferably from 15 to 18 bases. An "antisense" oligo includes a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length. One of skill in the art can easily choose and synthesize any of a number of appropriate antisense molecules in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, an oligo includes a recognition sequence for a protein, e.g., for a transcription factor. A number of DNA-binding proteins, including transcription factors, and their recognition sequences, are known in the art. A list of Examples is included herein in Table 1.

TABLE 1

Exemplary Transcription Factors

| Factor | Recognition Sequence | SEQ. ID NO.: |
|---|---|---|
| c-Myc and Max | CACGTG | 18 |
| c-Fos and c-Jun | TGA$^{C}/_{G}$T$^{C}/_{A}$A | 9 |
| CREB | TGACG$^{C}/_{T}$$^{C}/_{A}$$^{G}/_{A}$ | 10 |
| c-ErbA and TR (thyroid hormone receptor) | GTGTCAAAGGTCA | 11 |
| c-Ets | $^{G}/_{C}$$^{A}/_{C}$GGA$^{A}/_{T}$G$^{T}/_{C}$ | 12 |
| GATA | $^{T}/_{A}$GATA | 13 |
| c-Myb | $^{T}/_{C}$AAC$^{G}/_{T}$G | 14 |
| MyoD | CAACTGAC | 15 |
| NF-κB and c-Rel | GGGA$^{A}/_{C}$TN$^{T}/_{C}$CC$^{(1)}$ | 16 |
| RAR (retinoic acid receptor) | ACGTCATGACCT | 17 |

Detectable Reporter Groups

Various fluorescent or quenching reporter groups can be covalently attached to the amino groups of the synthesized oligonucleotides in high yields, e.g., for optical sensing the oligos, e.g., for measuring nucleic acid-nucleic acid or protein-nucleic acid interactions, e.g., protein-DNA interactions.

A number of suitable reporter groups are known in the art, e.g., fluorochromes such as quantum dots and near infrared dyes, including but not limited to: Cyanine dyes (e.g., Cy2, Cy3, Cy3.5, Cy5, and Cy5.5, available from Amersham Life Sciences Inc., Piscataway, N.J.); IR dyes (e.g., IRDye 680, IRDye 700, IRDye 800, IRDye 800CW, IRDye 800RS, and IRDye 700DX, available from Li-COR, Lincoln, Nebr.), and Alexa Fluor Dyes (e.g., Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, and Alexa Fluor 750, available from Invitrogen, Carlsbad, Calif.).

In some embodiments, e.g., where the nucleosides or oligos are intended to be used with a fluorescence resonance energy transfer (FRET) method for detecting molecular interactions, a quencher group can be used. For example, the QSY dyes (e.g., QSY 7, QSY 9, QSY 21, and QSY 35, from Invitrogen) are non-fluorescent and have broad absorption wavelengths covering the visible spectrum and can serve as efficient quenchers of the fluorescence emission from almost any blue-, green-, orange- or red-fluorescent dyes, including the Alexa Fluor dyes. The selection of suitable acceptor-donor pairs of dyes for use in FRET methods is known in the art.

Fluorescent proteins and FRET pairs of fluorescent proteins (for example, yellow and green fluorescent proteins), as well as non-quenched quantum dots or quantum dot pairs can also be used in combination with amino-linked nucleosides or oligos of the invention.

Non-fluorescent groups can also be used, e.g., tags (reporter ligands such as biotin, digoxigenin), adapter proteins such as (strept)avidin, magnetic and non-magnetic colloids and nanoparticles such as iron oxides, magnetites, gold and silver colloids, or reporter enzymes such as horseradish peroxidase or lactase, and the latter can be used in combination with chromogenic substrates.

Chemical Groups

Chemical groups that could be linked to the linker moiety could include peptides or polyethylene glycol moieties. Peptides could contain from about 2 to 100 amino acids. The amino acids can be any of the natural or unnatural amino acids. Polyethylene glycol (PEGs) moieties are often included for enhancing drug delivery. PEGS could be of varying molecular weights due to their varying chain lengths. Such PEGs display desirable properties depending on the chain length.

Attachment to Solid Surfaces

The linker moieties described herein can be used to attach the nucleoside analogs, or oligos comprising the nucleosides, to a solid surface. For example, the linkers can be used to attach the oligos to a magnetic bead, or to the surface of a glass or plastic coverslip. Since the linkers described herein can be placed in the middle of an oligo, this allows the attachment of the oligo in an orientation more parallel to the surface, rather than at either end as is more commonly the case. Of course, the linkers can also be placed at the end of the oligo. The solid surface-linked nucleosides can be used for synthesizing random or non-random oligonucleotide and aptamer libraries or arrays for identification of novel DNA-binding proteins or for protein engineering of DNA-binding motifs, or for selecting DNA-binding small molecules.

Methods of Synthesis of Oligonucleotides

The nucleoside analogs described herein can be used in known methods of oligonucleotide synthesis, to obtain oligos including one or more of the analogs described herein. One or more of the analogs can be incorporated, e.g., during synthesis, e.g., during automated synthesis, at one or more positions in the oligo. For example, the analogs can be at one or more of the alpha position, the omega position, or any internal position along the backbone.

A number of methods for performing oligonucleotide synthesis are known in the art, see, e.g., U.S. Pat. Nos. 7,227,017; 7,019,127; 6,531,589; 6,040,439; 6,506,894; 6,429,309; 4,458,066; 4,500,707; 4,753,985; 4,795,700; 4,973,679; 5,026,838; 5,047,524; 5,132,418; RE34069; 5,164,491; 5,216,141; 5,362,866; 5,407,795; 5,510,476; 5,514,789; 5,548,076; 5,554,746; 5,614,621; 5,705,621; 5,714,597; 6,096,881; 6,111,086; 6,465,628; 6,768,005; 6,858,715; 7,041,816; 2006/0036028; EP 0 323 152; EP 0 288 310; EP 1 028 124; JP 2003/238586 WO 92/09615; WO 94/01446; WO 97/40458; WO 00/20431; WO 00/46231; WO 01/27126; WO 01/96358; Gait (ed.), *Oligonucleotide Synthesis—A Practical Approach* (IRL Press, Washington, D.C., 1984) (incorporated in its entirety), and references cited in each of these.

Uses

The oligonucleotides described herein have a number of uses. For example, oligos comprising a fluorescent or quenching reporter group can be used to evaluate nucleic acid-protein interactions as described herein. In addition, the synthons described herein can be used to synthesis therapeutic oligonucleotides, e.g., therapeutic RNAs or DNAs, e.g., small interfering RNAs. The oligonucleotides described herein display enhanced uptake into cells when compared to oligos lacking the described linkers. Thus, the methods can be used to enhance delivery of a therapeutic oligonucleotide to a target cell, e.g., in vivo or in vitro.

Pharmaceutical Compositions

The methods described herein include the manufacture and use of pharmaceutical compositions, which include compounds described herein (i.e., nucleoside analogs and oligos comprising the analogs) as active ingredients. Also included are the pharmaceutical compositions themselves, and pharmaceutically acceptable salts of the compounds described herein. It is well known in the pharmacological arts that nontoxic addition salts of pharmacologically active amine compounds do not differ in activities from their free base.

Pharmaceutically acceptable salts include both acid and base addition salts. "Pharmaceutically acceptable salt" refers to those salts which retain the biological effectiveness and properties of the free bases and which are not biologically or otherwise undesirable. Suitable pharmaceutically acceptable acid addition salts can be formed with inorganic acids such as hydrochloric acid, hydrobromic acid, sulfuric acid, nitric acid, phosphoric acid, and the like, and organic acids such as acetic acid, propionic acid, glycolic acid, pyruvic acid, fumaric acid, tartaric acid, citric acid, benzoic acid, cinnamic acid, mandelic acid, methanesulfonic acid, and p-toluenesulfonic acid, and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines, including naturally occurring substituted amines, cyclic amines and basic ion exchange resins, such as isopropylamine, tripropylamine, ethanolamine, 2-diethylaminoethanol, 2-dimethylaminoethanol, dicyclohexylamine, lysine, arginine, histidine, caffeine, procain, hydrabamine, choline, betaine, ethylenediamine, glucosamine, methylglucamine, theobromine, purines, piperazines, piperidine, polyamine resins and the like. Particularly preferred organic non-toxic bases are isopropylamine, diethylamine, ethanol-amine and dicyclohexylamine.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims.

Example 1

Synthesis of 5"-O-DMTr-thymidine-3"-O-(2-(2-(2-trifluoroacetamido ethoxy)ethoxy)ethyl)-N,N-diisopropylphosphoramidite (Synthon 2) (See FIG. 4)

To introduce one or more amino groups attached by an appropriate linker to the internucleoside phosphate group in a position specific manner, using standard phosphoramidite chemistry with no post-synthetic modifications, a phosphoramidite synthon was designed: 5'-O-DMTr-thymidine-3'-O-(2-(2-(2-trifluoroacetamidoethoxy)-ethoxy)ethyl)-N,N-diisopropylphosphoramidite. The 9 atom, triethylene glycol linker was expected to have minimal tendency to undergo cyclization by a nucleophilic attack of the terminal amino group on the carbon atom adjacent to the phosphate group (i.e. undergo β-elimination). In addition, the polyethylene glycol spacers are hydrophilic in nature, conformationally flexible in both organic and aqueous environments, and are biologically inert (Greenwald et al., (2000) Critical Rev. Ther. Drug Carrier Systems, 17, 101-161; Zalipsky (1995) Bioconjugate Chem., 6, 150-165). The trifluoroacetyl protection of the amino group was chosen due to its stability under the automated oligonucleotide synthesis conditions, and easy removal during the basic deprotection of the oligonucleotide. The synthon was synthesized with the yield of 40% and characterized using proton and $^{13}$C-NMR spectroscopy.

The synthesis of amidite 2 is outlined in FIG. 4. First, commercially available 2-(2-(2-chloroethoxy)ethoxy)ethanol, was converted, via the azide, to 2-(2-(2-aminoethoxy)ethoxy)ethanol, in a one pot synthesis in 88% yield. Briefly, a mixture of 2-(2-(2-chloroethoxy)ethoxy)ethanol (50.0 g, 0.297 mol) and sodium azide (19.28 g, 0.297 mol) in 450 ml N,N-dimethylformamide was stirred overnight at 90° C. The mixture was cooled, diluted with 500 ml tetrahydrofuran, and, after stirring for 1 hour, was filtered. The solid salts were washed with tetrahydrofuran. The combined filtrate and washings, which contain the azide were stirred and treated with triphenylphosphine (83.76 g, 0.319 mol), added in two portions, and stirring protected from the atmosphere for 48 hours. Water (8.1 ml) was added, and stirring was continued for another 48 hours. The mixture was evaporated on a membrane pump vacuum, and then on an oil pump vacuum, at a bath temperature of 45° C. The residue was stirred with 850 ml of water and filtered. The solid was washed with water, and the combined filtrate and washings were concentrated on a membrane pump vacuum at a bath temperature of 70° C. The resulting yellowish oil was distilled under vacuum (0.2 mm Hg) to give 2-(2-(2-aminoethoxy)ethoxy)ethanol as a colorless oil: 39.3 g, 88% yield. $^1$H NMR (CDCl$_3$): δ 3.54-3.72 (m, 8H, CH$_2$—O), 3.51 (t, 2H, CH$_2$—OH), 2.82 (t, 2H, CH$_2$—NH$_2$), 2.30 (bs, 3H, NH$_2$+OH); $^{13}$C NMR (Me$_2$SO-d$_6$): δ

73.82, 73.24, 70.63, 70.49, 61.06, 42.14; ESI+MS: [M+H]+ 150.3, calculated for $C_5H_{16}NO_3$ 150.2.

The amino group of 2-(2-(2-aminoethoxy)ethoxy)ethanol was protected as the trifluoroacetamide by reaction with excess of methyl trifluoroacetate to give in 98% yield. Briefly, methyl trifluoroacetate (3.20 g, 2.52 ml, 25 mmol) was added dropwise through a septum with stirring and gentle cooling to 2-(2-(2-aminoethoxy)ethoxy)ethanol (2.98 g, 20 mmol), and the mixture was sealed and left at room temperature for 24 hours. The volatiles were evaporated under membrane pump vacuum and bath temperature of 65° C. to give trifluoro-N-(2-(2-(2-hydroxyethoxy)ethoxy)ethyl)acetamide as a slightly yellowish oil which crystallized when stored in the refrigerator: 4.83 g, 98% yield. $^1H$ NMR (DMSO-$d_6$): δ 9.41 (t, 1H, NH), 4.57 (bs, 1H, OH), 3.55-3.28 (m, 12H, $CH_2$); $^{13}C$ NMR (DMSO-$d_6$): δ 156.60 (q, J=36.1 Hz, CO), 115.96 (q, J=116 Hz, $CF_3$), 73.15, 70.50, 70.46, 68.67, 61.08, 39.99.

Next, the diamidite was prepared by reaction of with bis(diisopropylamino)-chlorophosphine and diisopropylamine, and, without isolation, was converted to the targeted amidite by reaction with a slight excess of 5'-O-DMTr-dT in the presence of tetrazole. Briefly, bis-(diisopropylamino)chlorophosphine (1.334 g, 5 mmol) was weighed in an argon-filled glove bag and loaded in a flame-dried, cooled under argon vial equipped with a stirring bar. The vial was sealed with a Teflon-lined septum, and 20 ml of dry benzene were added through the septum under argon, followed by dry diisopropylamine (0.607 g, 0.848 ml, 6 mmol). The clear solution was cooled to 10° C., and a solution of (1.23 g, 5 mmol) in 2.6 ml of dry benzene was added dropwise with vigorous stirring and cooling during ca. 3 minutes. The mixture was stirred under argon for 1 hour at room temperature. At that time a $^{31}P$ NMR spectrum of the reaction mixture showed complete consumption of bis-(diisopropylamino)chlorophosphine. The reaction mixture was filtered under positive pressure of argon through a glass fiber filter, and the solid was washed with dry benzene. The combined filtrate and washings were evaporated under membrane vacuum to yield as an oil. The oil was dissolved in 10 ml of dry N,N-dimethylformamide, and the solution was added through a septum to 5'-O-DMTr-thymidine (3.00 g, 5.5 mmol) in an argon-filled, flame dried flask, followed by 3 ml of a 0.45 M tetrazole solution in dry acetonitrile. This mixture was stirred for 1 hour under argon at room temperature. Triethylamine (0.5 ml) was added, and the reaction mixture was evaporated under vacuum. The resulting oil was dissolved in 50 ml dichloromethane and loaded onto a silica gel column (30×5 cm), equilibrated with hexane:ethyl acetate: triethylamine, 66:33:2, and eluted with a gradient of hexane: ethyl acetate:triethylamine, 66:33:2, to ethyl acetate:triethylamine, 100:2 (4 l), at a flow rate of 50 ml/minutes. The fractions containing 2 were pooled and evaporated to give 2.40 g of solid. This material was 95% pure by HPLC and contained 1.7 mol % of bis-(DMTr-T)-N,N-diisopropylphosphoroamidite. Because this impurity can cause branching during oligonucleotide synthesis, the product was repurified on a silica gel column which was eluted first with an isocratic mixture of hexane:ethyl acetate:triethylamine, 59:39:2, (2 l), and then with a gradient of hexane: ethyl acetate:triethylamine, 59:39:2,—hexane:ethyl acetate:triethylamine, 39:59: 2, (4 l). The fractions containing pure 2 were pooled and evaporated under vacuum. The residue was dissolved in dry benzene and lyophilized to give 1.84 g (40% yield) of 6 as a colorless powder. HPLC: two diastereomers in ratio 2:1; purity, 96% and no bis-(DMTdT)-phosphoramidite contamination. $^1H$ NMR ($C_6D_6$): δ 10.3 (bs, 1H, NH-1), 7.8-7.5 (m, 4H, H-6+Ar—H+NH), 7.48-7.37 (m, 4H, Ar—H), 7.25-7.15 (m, 2H, Ar—H), 7.13-7.04 (m, 1H, Ar—H), 6.83-6.75 (m, 4H, Ar—H), 6.65-6.53 (m, 1H, H-1'), 4.86-4.76 (m, 1H, H-4'), 4.33 and 4.18 (2 m in ratio 2:1, 1H, H-3'), 3.83-3.20 (m, 16H, $CH_2O$, $CH_2NH$, H-5'5", $NCHMe_2$), 3.37 (s, 6H, $CH_3O$), 2.64-2.26 (m, 2H, H-2'2"), 1.56 (s, 3H, 5-Me), 1.18-1.02 (12H, $CHMe_2$); $^{13}C$ NMR ($C_6D_6$): δ 164.82$^b$, 164.75$^a$; 159.73$^a$, 159.71$^b$; 157.64 (q; $^2J_{C-F}$=36.1 Hz), 157.60$^a$ (q; $^2J_{C-F}$=36.1 Hz); 151.52$^b$, 151.48$^a$; 145.65$^a$, 145.55$^b$; 136.37; 136.32$^b$, 136.00$^a$; 131.01; 129.07; 128.92; 128.63; 127.72; 117.13$^b$ (q; $^1J_{C-F}$=288.0 Hz), 117.18 (q; $^1J_{C-F}$=288.0 Hz); 114.04; 111.57; 110.22; 87.67; 86.33a (d; $^3J_{C-P}$=4.0 Hz), 86.01$^b$ (d; $^3J_{C-P}$=6.3 Hz); 85.72; 74.00$^a$ (d; $^2J_{C-P}$=15.5 Hz), 73.89$^b$ (d; $2J_{C-P}$=17.2 Hz); 71.86$^b$ (d; $^3J_{C-P}$=6.9 Hz), 71.79$^a$ (d; $^3J_{C-P}$=7.4 Hz); 71.11$^b$, 71.05$^a$; 70.76$^b$, 70.71$^a$; 64.08$^a$, 63.87$^b$; 63.46$^b$ (d; $^2J_{C-P}$=16.1 Hz), 63.33$^a$ (d; $^2J_{C-P}$=16.6 Hz); 55.25; 43.76 ($^2J_{C-P}$=12.6 Hz); 40.90$^b$ (d; $3J_{C-P}$=3.4 Hz), 40.60$^a$ (d; $^3J_{C-P}$=4.6 Hz); 40.35$^b$, 40.27$^a$; 25.06; 24.97; 12.25; $^{31}P$ NMR ($^1H$ dec., $C_6D_6$): δ 149.69, 149.51 (s, in ratio 1:2); Most of the $^{13}C$ resonances are split due to the presence of two diastereomers in ratio 2:1. In those cases the signal associated with the more abundant diastereomer is indicated with the superscript "a", and the signal due to the less abundant diastereomer—with the superscript "b". $^{19}F$ NMR ($^1H$ dec., $C_6D_6$): δ–75.86, –75.92 (s, in ratio 1:2); ESI+MS: [M+Et$_3$NH]+ 1020.23, calculated for $C_{51}H_{74}F_3N_5O_{11}P$ 1020.51; ESI– MS: [M–H]– 917.50, calculated for $C_{45}H_{57}F_3N_4O_{11}P$ 917.37.

Thus, synthon 2 was isolated in 52% yield and 95% purity by silica gel chromatography. This material was repurified to remove a small amount (1.7 mol %) of (DMTr-T)$_2$PN(i-Pr)$_2$, which could cause branching during oligonucleotide synthesis, to give, after lyophilization from benzene, 2 in 40% final yield.

Example 2

Stability and Coupling Efficiency of Synthon 2

After storing synthon 2 for six months at –20° C., no apparent decrease in coupling efficiency was detected. Usually the compound was dissolved in anhydrous acetonitrile under argon and was kept on the synthesizer for up to two weeks at room temperature. The coupling yield of the monomer for the 3 minutes coupling duration was 98-99% after 7-8 days, and for the same coupling conditions coupling yield decreased to 90% after additional 10-12 days. Coupling yields were assessed using a DMTr detector reading on the synthesizer. Based on this finding it was concluded that dry monomer stored at –20 C preserves its intactness over six months and is stable in dry acetonitrile for at least one week.

Example 3

Oligonucleotide Synthesis

Briefly, synthesis of oligonucleotides was performed using phenoxyacetyl protected dA, 4-isopropyl-phenoxyacetyl protected dG, acetyl protected dC and dT phosphoramidites (all from Glen Research, Sterling Va.) on a 394 DNA/RNA synthesizer (Applied Biosystems) by using a standard protocol for phosphoramidite synthesis. Synthesis was performed on 1 μM dT-CPG (controlled pore glass) columns (Glen Research). Coupling duration for the incorporation of the novel dT phosphoramidite monomer 2 at the targeted location of the oligonucleotide sequence was increased up to 3 minutes. A 50 mM solution of monomer in anhydrous acetonitrile was used. Coupling efficiency according to the DMTr monitor reading was 99%. Deprotection of oligonucleotides was carried out for 5 hours at room temperature using concentrated ammonium hydroxide. Four oligonucleotides containing either one (I-III) or two (IV) internucleoside aminolinkers were synthesized (Table 2).

Initially the synthesis of an oligonucleotide was attempted by combining standard phosphoramidite monomers (benzoyl protected dA and dC, and iso-butyryl protected dG) with the thymidine phosphoramidite synthon, 2. The average coupling yield for 2 was 96-97% under standard conditions. When coupling time was increased up to 3 minutes, the coupling efficiency increased to 99%. The HPLC analysis after standard deprotection showed that a major portion of the final product was cleaved into several small fragments. Since phosphotriesters are less stable in basic environment than phosphodiesters (Caruthers et al., (1987) Methods Enzymol., 154, 287-313; Bannon and Verly, (1972) Eur. J. Biochem., 31, 103-111) "ultramild" phosphoramidite monomers (phenoxyacetyl protected dA, 4-isopropyl-phenoxyacetyl protected dG and acetyl protected dC from Glen Research) were used. The use of "ultramild" monomers enabled deprotection under milder conditions (5 hours of ammonium hydroxide treatment at room temperature instead of 14-16 hours at 55° C.), which resulted in a great improvement of the yield of the final product. The wide applicability of internucleotide amino linkers was demonstrated by synthesizing four 19-mer oligonucleotides containing one or two amino linker groups at different positions (See Table 2). Also, for comparison purposes, few 19-mer oligonucleotides (such as oligonucleotide V in Table 2) were synthesized using a commercial G-phosphoramidite monomer with an amino group attached through an aminohexyl linker to C-8 of the base.

Ion-paired reverse phase HPLC on a C18 column was used for the isolation and post-deprotection purification of the modified oligonucleotides, using a C18 column (Microsorb-MV 100-5, 250×4.6 mm, Varian, Palo Alto Calif.). For the linear eluting gradient the following buffers were used: A, 2% acetonitrile in 0.1 M triethylammonium acetate (TEAA), pH 7 (Glen Research); B, 50% acetonitrile in 0.1 M TEAA, pH 7. The column was eluted at 1 ml/minute at room temperature. To isolate trityl-on oligonucleotides the following gradient was used: 90% A-10% B for 3 minutes, then to 100% B in 22 minutes. Detritylation was performed by treating with 80% acetic acid for 30 minutes followed by ethanol/sodium acetate precipitation. The purity of obtained oligonucleotides was determined by reverse phase HPLC using a gradient of 90% A-10% B for 3 minutes, then to 50% A-50% B in 47 minutes.

Purity and identity of the products were determined by analytical reverse phase HPLC and ESI mass spectrometry (See Table 2).

Watson-Crick base paring properties of the modified oligonucleotides were evaluated by comparison of melting temperatures of a duplex formed between the amino-functionalized oligonucleotide CGG AAA GT*C CCT CAT AGC T (I, SEQ ID NO: 1) and its complementary unmodified oligonucleotide 3'GCC TTT CAG GGA GTA TCG A 5' (Duplex 1, SEQ ID NO:5) and a control, unmodified duplex with the same sequence (Duplex 2). The melting temperatures were almost equal, i.e. 65 and 66° C. for Duplexes 1 and 2, respectively. Therefore, the presence of an aminolinker phosphotriester group in the middle of the oligonucleotide sequence did not interfere with Watson-Crick hybridization properties of the oligonucleotides.

TABLE 2

Synthesized oligonucleotides bearing one or two amino reporter groups at various positions and the corresponding dye-conjugated products.

| # | SEQ ID NO: | Oligonucleotides[a] | Molecular mass calculated | observed[b] |
|---|---|---|---|---|
| I | 1 | CGGAAAGT*CCCTCATAGCT | 5904.0 | 5904.2 |
| II | 2 | TGGAAAGCTTTT*TACAGTT | 5964.1 | 5964.4 |
| III | 2 | TGGAAAGCTTTCTAT*AGTT | 5964.1 | 5965.2 |
| IV | 2 | TGGAAAGCTTTT*TAT*AGTT | 6110.3 | 6111.6 |
| V | 3 | CGGAAAG^TCCCTCATAGCT | NA | |
| VI | 3 | CGGAAAGT[Cy3.5]CCCTCATAGCT | NA | |
| VII | 3 | CGGAAAGT[QSY21]CCCTCATAGCT | NA | |
| VIII | 3 | CGGAAAGT[800CW]CCCTCATAGCT | 6888.9 | 6888.0 |
| IX | 3 | CGGAAAGT[Cy7]CCCTCATAGCT | NA | |
| X$_1$ | 3 | CGGAAAGT[dabcyl]CCCTCATAGCT (fraction 1) | 6155.8 | 6155.6 |
| X$_2$ | 3 | CGGAAAGT[dabcyl]CCCTCATAGCT (fraction 2) | 6155.8 | 6155.4 |
| XI | 2 | TGGAAAGCTTTT[800CW]TACAGTT | 6949.0 | 6950.0 |
| XII | 2 | TGGAAAGCTTTT[dabcyl]TACAGTT | 6215.3 | 6216.0 |
| XIII | 2 | TGGAAAGCTTTT[Cy7]TACAGTT | NA | |
| XIV | 2 | TGGAAAGCTTTCTAT[dabcyl]AGTT | 6215.3 | 6216.4 |

TABLE 2-continued

Synthesized oligonucleotides bearing one or two amino reporter groups at various positions and the corresponding dye-conjugated products.

| # | SEQ ID NO: | Oligonucleotides[a] | Molecular mass calculated | Molecular mass observed[b] |
|---|---|---|---|---|
| XV | 2 | TGGAAAGCTTTCTAT$^{800CW}$AGTT | 6949.0 | 6950.0 |
| XVI | 2 | TGGAAAGCTTTT$^{dabcyl}$TAT$^{dabcyl}$AGTT | 6612.8 | 6613.2 |
| XVII | 1 | CGGAAAG$^{800CW}$TCCCTCATAGCT | 6870.9 | 6870.8 |
| XVIII | 4 | AGCTATGAG$^{800CW}$GGACTTTCCG | 6942.9 | 6942.0 |
| XIX | 4 | AGCTATGAGGGACTTTCCG-Y | 6087.9 | 6087.6 |

[a] T* is T-O-P(=O)-OCH$_2$CH$_2$OCH$_2$CH$_2$OCH$_2$CH$_2$NH$_2$;
T$^{Cy3.5}$ is T-O-P(=O)-OCH$_2$CH$_2$OCH$_2$CH$_2$OCH$_2$CH$_2$NH-Cy3.5;
T$^{QSY21}$ is T-O-P(=O)-OCH$_2$CH$_2$OCH$_2$CH$_2$OCH$_2$CH$_2$NH-QSY21;
T$^{800CW}$ is T-O-P(=O)-OCH$_2$CH$_2$OCH$_2$CH$_2$OCH$_2$CH$_2$NH-800CW;
T$^{dabcyl}$ is T-O-P(=O)-OCH$_2$CH$_2$OCH$_2$CH$_2$OCH$_2$CH$_2$NH-dabcyl;
T$^{Cy7}$ is T-O-P(=O)-OCH$_2$CH$_2$OCH$_2$CH$_2$OCH$_2$CH$_2$NH-Cy7;
Ĝ is -NH-(CH$_2$)$_6$-NH$_2$ at the 8 position of guanine;
G$^{800CW}$ is -NH-(CH$_2$)$_6$-NH-800CW at the 8 position of guanine;
Y is HO(CH$_2$)$_3$SS(CH$_2$)$_3$O-((O=(HO)P)-O- linker.
[b] by MS. NA, not analyzed.

Example 4

Oligoribonucleotide (ORN) Synthesis

Synthetic incorporation of thymidine synthon 2 of Example 1 in Oligoribonucleotide (ORN) Synthesis was performed by using 19-mer siRNA *P. pyralis* luciferase sense strand sequence with a 3'-end dithymidine overhang: 5'-CAUUAUAAAUAUCAUUCGCd(TT)-3' (SEQ ID NO:6).

Two variants were prepared without a loss of silencing activity: with one thymidine (U→T position #3) and two thymidines (positions #3 and 20)

The synthesis of oligoribonucleotides (ORN) was performed using 394 DNA/RNA synthesizer using 5'-DMT and 2'-TBDMS protection chemistry. A 5 minutes coupling step for 2'-O-t-butyldimethylsilyl protected nucleosides was used. A 7-fold excess of phosphoramidite and a 30-fold excess of 5-ethylthio-1H-tetrazole (Aldrich) relative to CPG-bound dT was used in each coupling cycle. For detritylation, 2% trichloroacetic acid in methylene chloride was used. For capping, 16% N-methylimidazole and 10% acetic anhydride/10% 2,6-lutidine in tetrahydrofuran (THF) were used; for oxidation 16.9 mM iodine in 49 mM pyridine, 9% water in THF were used, respectively. The deprotection of amino protecting groups and the cleavage of ORN off CPG carrier was accomplished by treating ORN with NH$_4$OH/methylamine 1:1 (by volume) at 65° C. for 10 minutes followed by incubating at −20° C. for 2 hours and removing the precipitate of CPG. The deprotection of 2'-O-silyl groups was accomplished by using anhydrous tetrabutylammonium fluoride I(TBAF)/N-methylpyrrolidinone (NMP) solution (TBAF in NMP, total 1.4 M HF) at 65° C. for 1.5 hours followed by quenching with 50 mM triethylammonium bicarbonate (TEAB) prior to the addition of 3 M sodium acetate followed by precipitating in n-BuOH. After the centrifugation, ORN precipitate was washed with 70% EtOH and then dried. Anion exchange desalting of the deprotected ORN was performed by using Qiagen 500® anion exchange cartridge pre-washed with 50 mM TEAB. After washing the loaded cartridge with 50 mM TEAB the ORN was eluted with 2 M TEAB.

Example 5

Conjugation of the Amino-Modified Oligonucleotides with Fluorescent Dyes

Amino-functionalized oligonucleotides were conjugated with three different red and far-red fluorochromes (Cy3.5, Cy7 and 800CW) as well as with two quenchers (dabcyl and QSY21).

Conjugation of oligonucleotides bearing aminolinkers with dabcyl and QSY21 NHS esters was performed as follows. Fifteen nmol of oligonucleotide bearing an aminolinker were dissolved in 40 µl of 0.1 M NaHCO$_3$. Three 10 µl portions of a saturated solution of dabcyl NHS ester (AnaSpec, San Jose, Calif.) in N,N-dimethylformamide were added to the oligonucleotide solution at 20 minute intervals, and the inhomogeneous mixture was left overnight at room temperature in the dark. Aqueous 2M LiClO$_4$ (0.1 ml) and 0.7 ml of acetone were added, the mixture was vortexed, and precipitates were collected after centrifugation at 10,000 rpm for 7 minutes. The oligonucleotides were then re-precipitated as above followed by Micro Bio-Spin 6 column (Bio-Rad Laboratories) purification according to the manufacturer's recommendations. After spin-chromatography, oligonucleotides were purified by reverse phase HPLC using the conditions described above. Purified oligonucleotides X, XII, XIV and XVI (Table 2) were concentrated in a centrifugal vacuum concentrator (SpeedVac, Savant) to 50-100 µl, and were precipitated by standard ethanol/sodium acetate treatment.

Conjugation of oligonucleotides bearing an aminolinker with Cy3.5, Cy7, or 800CW NHS esters was performed as follows. Ten nmol of aminolinker-bearing oligonucleotide were dissolved in 30 µl of 0.1 M NaHCO$_3$. Two 7.5 µl portions of dye solutions (0.5 mg in 30 µl dimethylsulfoxide; Cy3.5, Cy7 NHS esters were from Amersham-GE Healthcare (Piscataway N.J.), and heptamethine cyanine MRDye 800CW NHS ester was from Li-COR (Lincoln Nebr.)) were added over a 1 hour interval, and the homogeneous reaction mixture was left overnight at room temperature in the dark. The oligonucleotides were precipitated in a mixture of 0.1 ml water, 16 µl 3M sodium acetate (pH 5.5), and 0.7 ml ethanol. The mixture was left at −80° C. for 3 hours, and centrifuged at 10,000 rpm for 8.5 minutes. The labeled oligonucleotides VI, VIII, IX, XI, XIII, XV, XVII and XVIII (Table) were purified by spin-chromatography, then by reverse phase HPLC, and finally by ethanol/sodium acetate precipitation, as described above.

The conjugates were characterized by HPLC analysis, mass spectrometry and UV/VIS spectroscopy. Briefly, spectral measurements were performed using a Cary 50 Bio UV-visible spectrophotometer. Melting temperatures were determined with a step-wise Peltier temperature ramping bath in 2 degree mode in a temperature-controlled cuvette holder. Electrospray mass spectrometry (MS) was performed with a LTQ Linear Ion trap mass spectrometer (Thermo, Inc) with use of a Nanomate (Advion, Inc.) robot. Spectra were obtained in the negative ion mode with 1.8 kV spray voltage and 0.8 PSI back pressure (UMMS Proteomic and Mass Spectrometry Core Facility, University of Massachusetts Medical School, Worcester, Mass.). Sample solutions were adjusted to 75% methanol before MS analysis. The full mass spectra were acquired for 30 seconds from m/z 400-2000 using 2 ms scans and 10 ms maximum injection time.

The results of mass spectrometric analysis of the products correlated well with their calculated molecular masses (Table 2). HPLC analysis showed that covalent attachment of dyes to the aminolinker phosphotriester groups afforded high yields of target products (80-90%). For example, FIGS. 9A-B show HPLC profiles of CGGAAAGT$^{dabcyl}$CCCTCATAGCT (X, SEQ ID NO: 1) under conditions of steep and shallow gradients of acetonitrile, respectively. In the case of the shallow gradient the product X showed separation into two peaks. While not intending to be bound by theory, this separation is believed to be due to two different diastereomeric forms of the product as a result of creation of additional chiral center at the triester phosphorus atom. Those two peaks ($X_1$ and $X_2$) were collected separately, and their mass spectra were compared. The mass-to-charge values for both isomers were equal and in good agreement with the calculated masses of expected product (Table 2).

High yields of dye conjugation to the oligonucleotides at the internucleotide phosphotriester were observed for all compounds synthesized. While not intending to be bound by theory, the major factors explaining the high yields presumably are the steric accessibility and hydrophilic nature of the amino linker moiety. Covalent attachment of a dye to an aminolinker group at the internucleotide triester provided significantly higher yield than the attachment via an aminolinker of the heterocyclic base. FIGS. 10A-B show the HPLC analysis of the reaction mixtures resulting from labeling of CGGAAAG^TCCCTCATAGCT (V, SEQ ID NO:1) where the amino group is attached via hexylamino linker to C-8 of G and CGGAAAGT*CCCTCATAGCT (I, SEQ ID NO:1) where the amino group is attached to the phosphotriester, with IRDye 800CW NHS ester. Both reactions were performed at the same time and under identical conditions. Yield of VIII where dye is attached to the aminolinker at the phosphotriester (panel A, ~90%) was approximately 2.5 times higher than the yield of XVII where linking was performed via the aminolinker on the nucleotide base (panel B, ~35%). The same trend was observed in other experiments with NHS ester of heptamethine cyanine IRDye 800CW dye (the yield of XVIII was about 35%, however, the compounds XI and XV were obtained with the 85% yield) as well as with dabcyl NHS ester and the corresponding oligonucleotides.

Figure 12:
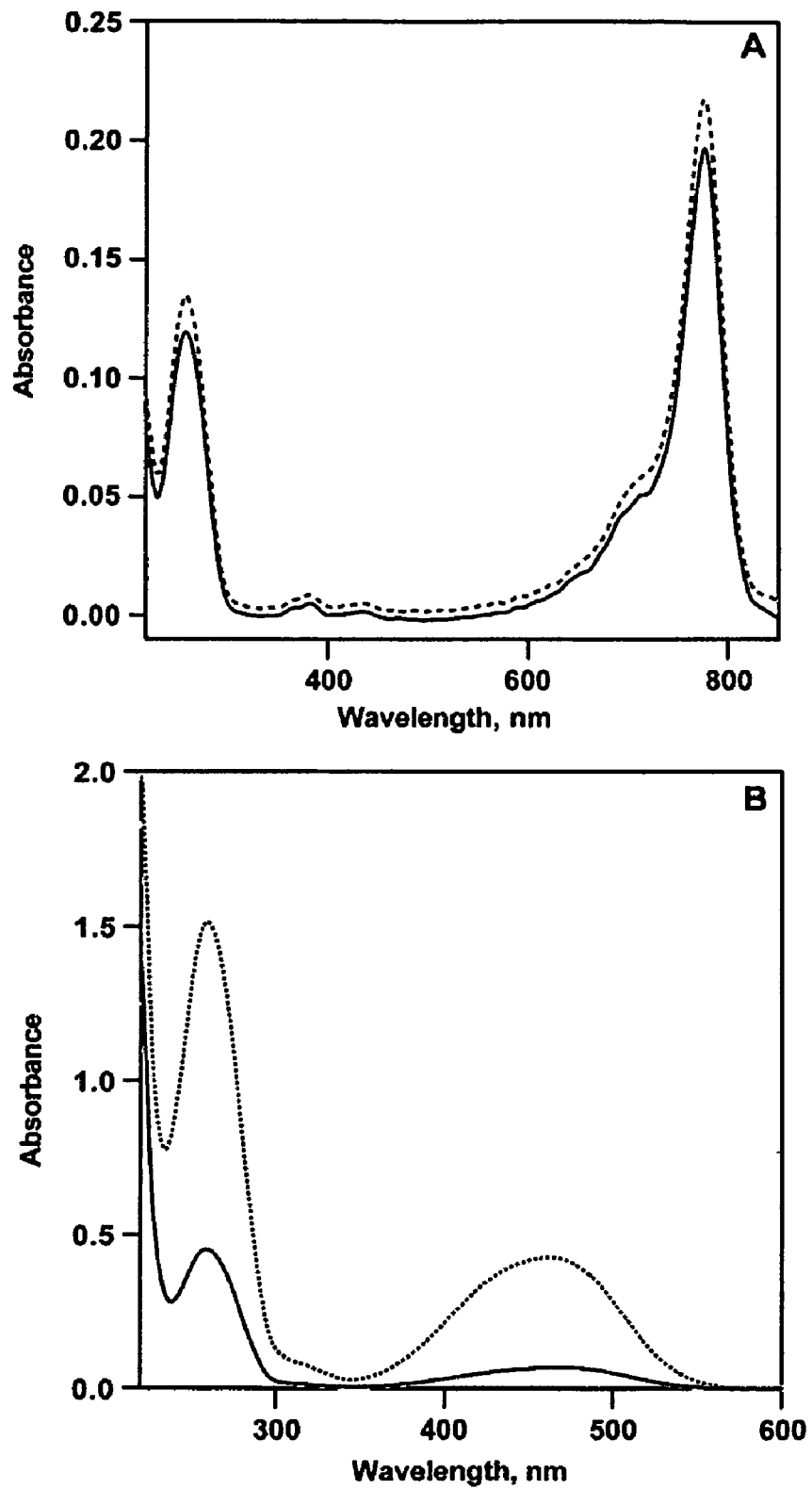
FIGS. 12A-B are line graphs showing UV/VIS spectra of dye-labeled oligonucleotides. 12A, CGGAAAGT$^{800CW}$CCCTCATAGCT (VIII, dotted line) (SEQ ID NO:3) and TGGAAAGCTTTT$^{800CW}$TACAGTT (XI, solid line) (SEQ ID NO:2). 12B, TGGAAAGCTTTC-TAT$^{dabcyl}$AGTT (XIV, solid line) (SEQ ID NO:2) and TGGAAAGCTTTT$^{dabcyl}$TAT$^{dabcyl}$AGTT (XVI, dotted line) (SEQ ID NO:2).

A di-amino-functionalized oligonucleotide was labeled successfully to give the doubly labeled oligonucleotide in 50% yield. FIG. 11 shows HPLC analysis of the reaction mixture of TGGAAAGCTTTT*TAT*AGTT (IV, SEQ ID NO:4) and dabcyl NHS ester. The chromatogram shows three major peaks that correspond to the starting material, the mono-adduct, and the target product TGGAAAGCTTTT$^{dabcyl}$TAT$^{dabcyl}$AGTT (XVI, SEQ ID NO:4), respectively. Further evidence for labeling of oligonucleotides was found by comparison of UV/VIS spectra of a mono and di-labelled oligonucleotides. In FIG. 12A are shown the UV/VIS spectra of CGGAAAGT$^{800CW}$CCCTCATAGCT (VIII, SEQ ID NO:1) and TGGAAAGCTTTT$^{800CW}$TACAGTT (XI, SEQ ID NO:2), in which the absorbance maximum at 780 nm indicates the presence of covalently attached 800CW dye. In FIG. 12B are the UV/VIS spectra of dabcyl-labelled TGGAAAGCTTTCTAT$^{dabcyl}$AGTT (XIV, SEQ ID NO:3) and TGGAAAGCTTTT$^{dabcyl}$TAT$^{dabcyl}$AGTT (XVI, SEQ ID NO:4), both of which show absorbance maxima at 470 nm, indicating the presence of dabcyl groups. As expected, the double-labeled oligonucleotide XVI has a twice higher 470/260 nm absorbance ratio than oligonucleotide XIV (FIG. 12B).

Figure 13:
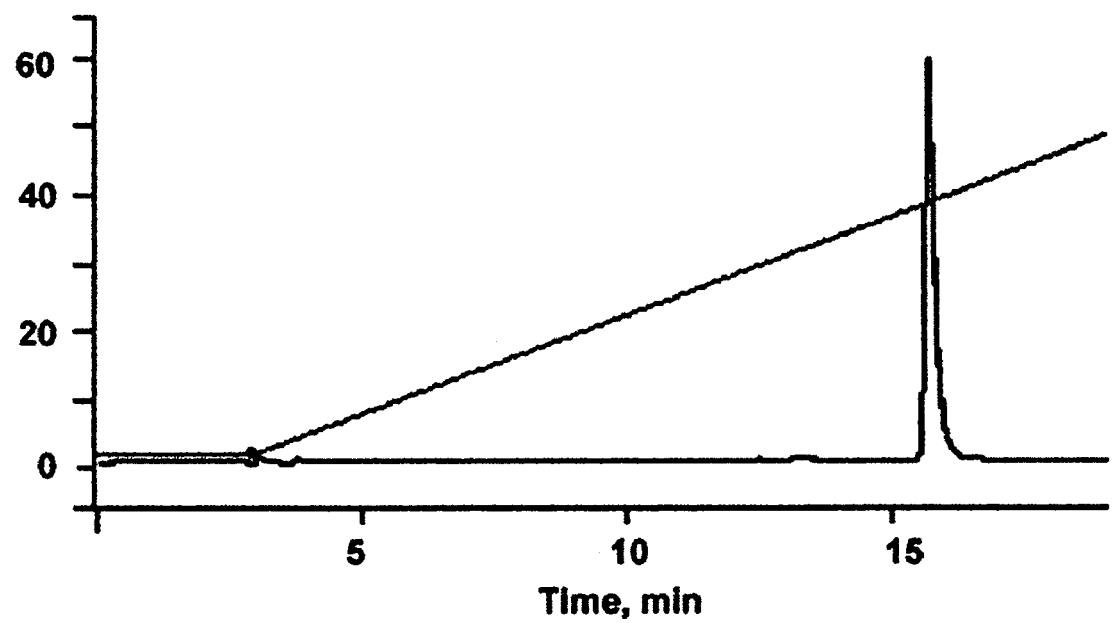
FIG. 13 is a line graph showing the results of reverse phase HPLC analysis of CGGAAAGT$^{800CW}$CCCTCATAGCT (VIII) (SEQ ID NO:3) dissolved in deionized water and stored at −20° C. for approximately 4 months.

A limited stability study of one of the novel oligonucleotide conjugates, VIII, which contained 800CW dye at the 8$^{th}$ nucleoside from the 5'-end (see Table 2), was performed. When dissolved in deionized water and stored at −20° C. for approximately four months, HPLC analysis showed no signs of degradation (FIG. 13).

These results demonstrate the synthesis and successfully use of a novel phosphoramidite synthon that enables facile incorporation of primary amino groups attached via a triethylene glycol linker to the internucleoside phosphates during the automated oligonucleotide synthesis. The novel aminolinker bearing oligonucleotides have preserved Watson-Crick base-pairing properties, are stable under deprotection and conjugation conditions, and are superior in their labeling yields to oligonucleotides containing base-attached aminolinkers. The novel synthon and ligand-conjugation method can be used for high yield, sequence-specific attachment of single or multiple ligands or reporter molecules to synthetic oligonucleotides.

Example 6

Fluorescence Resonance Energy Transfer (FRET) and Quenching in Duplex Probes

Two types of oligodeoxyribonucleotide (ODN) duplex probes were synthesized and tested for optical sensing of NF-κB p50 protein-DNA interactions using recombinant NF-κB p50 and IL-1beta activated human endothelial cells as model in vitro systems. The two types of probes tested were based on covalent linking of dyes to complementary ODNs: (1) Fluorescence resonance energy transfer (FRET) sensing probe based on energy transfer between Cy5.5 near-infrared fluorochrome as donor and 800CW as acceptor; and (2) quenched sensing probe based on Cy5.5 quenching with QSY 21.

The covalently labeled ODNs were synthesized by covalently linking either 800CW NHS ester, or QSY21 NHS ester to the ODN I and Cy5.5 linking via a reduced S—S bond to the 3' end of ODN XIX. The duplex probes were prepared using (1:1) molar ratios of ODNs: a) native, b) 800CW-I/Cy5.5-XIX (FRET probe; the numbers refer to the sequences shown above in Table 2), or c) QSY21-I/Cy5.5-XIX (quenched probe) were prepared by combining the ODNs at a 1:1 molar ratio (unless otherwise noted) in buffer solution containing 25 mM HEPES, 1 mM MgCl$_2$ and 50 mM NaCl.

The duplex mixtures were heated between 90-95° C. for 5 minutes to dissociate any intrastrand duplexes, and allowed to cool at room temperature.

The synthesized ODN duplex probes were characterized by comparing melting temperatures of native, non-modified ODN pair to those duplexes prepared by using covalently labeled ODNs. As shown in Table 3, by using TV spectroscopy and Cy5.5 fluorescence intensity measurements it was determined that the native duplex melts at higher temperature than 800CW-I/Cy5.5-XIX duplex (the difference—5° C.) but at approximately the same temperature as QSY21-I/Cy5.5-XIX duplex. Though the methods used for determining the melting temperatures (i.e. the temperatures corresponding to 50% strand separation) in native and covalently modified duplexes were different, the measurements of FRET loss in 800CW-I/Cy5.5-XIX duplex and de-quenching in QSY21-I/Cy5.5-XIX duplex suggest that linking of 800CW and Cy5.5 lead to a partial duplex destabilization, whereas QSY21 and Cy5.5 linking result in no destabilization, or even additional stabilization. The latter effect suggests that the fluorochrome and the quencher are capable of interacting with each other and that the observed quenching cannot be explained exclusively by the presence of non-radiative FRET effect.

The quenching of Cy5.5 fluorescence by QSY21 resulted in a more significant loss of Cy5.5 fluorescence than the decrease of Cy5.5 fluorescence as a result of energy transfer to 800CW dye (FIGS. 14A-B). FRET to a NIR acceptor resulted in 6-fold decrease of Cy5.5 fluorescence, whereas quenching resulted in a 25-fold decrease of Cy5.5 fluorescence intensity.

I/Cy5.5-XIX (FIG. 15C, trace 1). However, the kinetics of ExoIII-mediated QSY21-I/Cy5.5-XIX probe dequenching was slower (FIG. 15B) and the addition of QSY21-XIX ODN contributed to the dequenching delay, suggesting that Cy5.5 fluorochrome was accessible for interaction with QSY21 in solution.

To test whether the observed time delay of FRET loss in the presence of recombinant p50 and exonuclease activity could be used in detecting cells that express activated (processed) NF-κB transcription factor components (Baldwin, (1996) Annu. Rev. Immunol., 14, 649-683; Brand et al., (1997) Exp. Physiol., 82, 297-304; Baeuerle, and Henkel, (1994) Annu. Rev. Immunol., 12, 141-179), either control HUVEC or HUVECs treated with IL-1beta were used after incubation with 800CW-I/Cy5.5-XIX or QSY21-I/Cy5.5-XIX probes.

Briefly, human umbilical vein endothelial cells (HUVEC, subculture 2, (Gimbrone and Cotran, (1975) Lab. Invest., 33, 16-27)) were used. The cells were grown in 5% FBS, complete endothelial cell growth medium (EGM, Cambrex, Baltimore, Md.) until confluent. Cells were plated in the glass-coverslip chambers (Lab-Tek II, Electron Microscopy Sciences, Hatfield Pa.). Duplex probes were added to cells in 5% FBS/EBM at the final concentration of 1 μM and incubated at 37° C., 5% $CO_2$ for 4 hours. Cells were washed with 5% horse serum/PBS. Fluorescence images were acquired using Nikon TE2000-U inverted microscope equipped with a 100W Dia-illuminator and Nikon blue, Cy5, and 800 excitation fluorescence filter cubes. Images were acquired using CoolSnapHQ-M CCD (Photometrics, Tucson Ariz.). The results were processed using IP Lab Spectrum software (BD

TABLE 3

Oligonucleotide duplexes and their properties.

| Duplex | Duplex# | Melting point, ° C., (method) | FRET/ quenching efficiency |
|---|---|---|---|
| I/XIX | 5'-CGGAAAGT*CCCTCATAGCT-3' (SEQ ID NO: 1) 3'-YGCCTTTCAGGGAGTATCGA-5' (SEQ ID NO: 5) | 64 (UV) | N/A |
| 800CW-I/ Cy5.5- XIX | 5'-CGGAAAGT$^{800CW}$CCCTCATAGCT-3' (SEQ ID NO: 1) 3'-Cy5.5-S-GCCTTTCAGGGAGTATCG A-5' (SEQ ID NO: 5) | 59 (FRET) | 82.9 ± 2.3 |
| QSY 21-I/ Cy5.5- XIX | 5'-CGGAAAGT$^{QSY21}$CCCTCATAGCT-3' (SEQ ID NO: 1) 3'-Cy5.5-S-GCCTTTCAGGGAGTATCG A-5' (SEQ ID NO: 5) | 65 (dequenching) | 90.8 ± 4.0 |

For non-modified ODN: Y is $HOCH_2CH_2SSCH_2CH_2CH_2O-(O=(HO)P)-O-$
T* is $T-O-(P(OH)=O)-OCH_2CH_2OCH_2CH_2OCH_2CH_2NH_2$ The addition of human recombinant p50 protein that specifically binds to the NF-κB recognition sequence (5'-GGAAAGTCCC-3'; SEQ ID NO:8) resulted in a very rapid partial de-quenching of Cy5.5 fluorescence in QSY21-I/Cy5.5-XIX probe (FIG. 15A), and with the addition of an excess on QSY21-XIX ODN the relative dequenching of fluorescence was diminished. No such effect was observed if 800CW-I/Cy5.5-XIX probe was used instead. If Exo III was added to the reaction mixture containing p50 and the duplex probes (either QSY21-I/Cy5.5-XIX, FIG. 15B or 800CW-I/Cy5.5-XIX, FIG. 15C) a significantly delayed loss of FRET or de-quenching and the concomitant release of Cy5.5 fluorescence was observed in the presence of p50. In the absence of p50 the increase of Cy5.5 fluorescence due to the duplex degradation was almost instantaneous in the case of 800CW- Bioimaging, Rockville Md.). Region-of-interest analysis was performed by outlining the cell ROI using phase-contrast images and then pasting ROI for measuring fluorescence on 16-bit greyscale fluorescence images acquired using Cy5 and 800 filters. The ratios of 700/800 nm fluorescence were calculated and analyzed using Prism 4.0.

Flow cytometry was performed using FACScalibur (Beckton-Dickinson). Cells were treated with IL-1β (final concentration 2 pg/mL in EBM, Calbiochem, San Diego, Calif.) at 37° C. for 2 hours. The expression of E-selectin in response to IL-1beta treatment was detected by using anti-human E-selectin fragments H18/7 F(ab')$_2$ followed by FITC-labeled anti-mouse F(ab')$_2$ (10 μg/mL) diluted in 2% serum in Hanks' solution. Cells were washed and postfixed in 2% formaldehyde in buffered PBS before acquiring the images. Nuclear extracts and cytoplasmic extracts were prepared using HUVEC grown to 80% confluency. Control and IL-1β treated HUVEC cells were used. Cells were washed twice in 10 mL cold PBS and resuspended in 500 μL of buffer A (10 mM HEPES, 1.5 mM $MgCl_2$, 10 mM KCl, 0.5 mM DTT, 0.5 mM phenylmethylsulfonyl fluoride, 5 μg/mL leupeptin, 100 Hg/mL aprotinin, 1 μg/mL pepstatin) and incubated on ice for 15 minutes, followed by adding NP-40 to a final concentration of 0.5% and vortexing the cells for 10 seconds. The pellet was collected at 5,500×g, 20 seconds. The supernatant (cytoplasmic fraction) was transferred to a new tube. The nuclei pellet was resuspended in 150 μL buffer C (20 mM HEPES, 1.5 mM $MgCl_2$, 420 mM NaCl, 0.2 mM EDTA, 25% v/v glycerol, 0.5 mM phenylmethylsulfonyl fluoride, 5 μg/mL leupeptin, 100 μg/mL aprotinin, 1 μg/mL pepstatin), incubated on the ice for 30 minutes with agitation. Samples were centrifuged at 12,000 rpm for 10 minutes at 4° C., and the supernatant was removed and stored at −80° C. The protein concentration was determined by Micro BCA Protein Assay (Pierce, Rockford, Ill.).

The QSY21-I/Cy5.5-XIX probes resulted in very low cell fluorescence and the analysis of cell fluorescence intensity did not reveal any statistically significant differences between treated and control cells. In contrast, 800CW-I/Cy5.5-XIX FRET probe fluorescence allowed to localize Cy5.5 fluorescence distribution within the cells (FIGS. 16 A, B) and to register Cy5.5 channel fluorescence with green fluorescence resulting from cell surface labeling with anti-E selectin antibody fragments. Anti E-selectin H18/7 F(ab')$_2$ fragments stained IL-1beta activated cell plasma membranes and showed some internalization (compare FIGS. 16E and D). Anti E-selectin antibody fragments and 800CW-I/Cy5.5-XIX FRET probes were distributed in distinct intracellular compartments, i.e., no co-localization of green and red fluorescence in the cells was observed. Some staining of the nuclei was clearly present (see FIGS. 16A,B and E). Cells with the highest Cy5.5 NIR fluorescence (red, FIG. 16E) showed the lowest expression of E-selectin (green).

Furthermore, the expression of activated NF-κB transcription factor proteins was verified by performing electrophoretic mobility shift assays (EMSAs) in the presence of I/Cy5.5-XIX probe (i.e. non-FRET, always "on"). EMSAs were performed using a reaction mixture containing fluorescent and non-quenched I/Cy5.5-XIX duplex that was incubated for 30 minutes at room temperature in a volume of 10 μl in the presence of various concentrations of cell extracts in protein binding buffer (10 mM Tris, 100 mM KCl, 2 mM MgCl2, 0.1 mM EDTA, 0.1 mg/mL tRNA, 10% v/v glycerol, 0.25 mM DTT, pH 7.5). Samples were loaded and run on 10% TBE Ready Gels (Bio-Rad Laboratories, Hercules Calif.) with 0.5×TBE buffer. The gels were imaged and digitized using Odyssey Infrared Imaging system (Li-COR Biosciences, Lincoln Nebr.). The assay showed a concentration-dependent protein binding and shifting of the duplex in the presence of both nuclear and cytoplasmic protein fractions prepared from IL-1beta treated cells (see FIG. 16F, lanes 3, 4 and 6, 7). Very low levels of EMSA signal were observed in the presence of the control extracts (see FIG. 16F, lanes 2 and 5). In both nuclear and cytoplasmic protein extracts EMSA band fluorescence intensity signals in IL-1 beta treated cells were 8-10 times higher than in control experiments (control-2-3% and in experiment—22-24% of total fluorescence per lane).

Measuring the ratios of fluorescence intensities at 700 (Cy5.5) and 800 nm (800CW) was used to detect 800CW-I/Cy5.5-XIX FRET probe protection from degradation in live IL-1beta stimulated endothelial cells (FIG. 17A). The differences between ratio values in treated and control (non-treated cells) were statistically significant ($p<0.001$) only in control cells incubated with 800CW-I/Cy5.5-XIX. The microscopy quantitation results above were corroborated by using high-sensitivity NIR fluorescence measurements of cell suspensions in 96-well plates (FIG. 18A-B). HUVECs incubated with the non-FRET duplex probe (I/Cy5.5-XIX) showed the uptake of fluorescence that was independent of cell treatment with IL-1β, FIG. 18A). However, if a FRET reporter was used, the non-treated cells had a higher Cy5.5 fluorescence intensity than the IL-1β treated ones (FIG. 18B) at various numbers of cells used in the assay. The tendency of Cy5.5 fluorescence to increase in control cells incubated with 800CW—I/Cy5.5-XIX duplex probe was the opposite to that observed using QSY21-I/Cy5.5-XIX probe in HUVEC cells. Quenched probe behavior in cells suggested that IL-1beta treatment resulted in measurable but statistically insignificant fluorescence increase of Cy5.5 (FIG. 17B).

Cy5.5 fluorescence distribution was localized within the cells due to fluorescence changes in the 800CW-I/Cy5.5-XIX FRET reporter (FIGS. 16A-B). Some accumulation of the duplex in cell nuclei was clearly present. These experiments in HUVEC culture show that duplex reporters were taken up in cells. The highly sensitive NIR fluorescence measurements with the non-FRET duplex probe (I/Cy5.5-XIX) showed that the intake was the same irrespective of the presence of IL-1β (FIG. 18A). This cellular uptake was not dependent on the activation of cells by IL-1β, i.e., the transport of the duplex probes were possible. This transport could either be an active or a passive transport. The electrophoretic mobility shift assay clearly demonstrated that the cytoplasm of IL-1β treated cells contained high amounts of active p50 protein that binds to the duplex reporters (FIG. 16F).

These results demonstrated the potential of specific protein-mediated effects on the interacting pair of fluorochromes as well as protective effect of the specific binding against probe degradation as two promising approaches in designing sensing probes for imaging the activation of transcriptional factors in living cells. The ODNs enabled formation of either NIR FRET between the covalently linked dyes, or, alternatively, the formation of quenched dye pairs. The in vitro characterization of quenched probe suggested that it is useful in detecting transcription factors in homogenous assays. The results demonstrated that the optimization of design of the quenched probe with a more robust fluorescence increase due to the dye-quencher pair destabilization can potentially enable the direct detection of protein binding. In contrast, NIR FRET probes can be used as the ratiometric reporters of intracellular degradation and could sense the effect of specific protein-duplex interactions with the probe as endogenous exonuclease-mediated process. Similar probe designs are expected to be useful in detecting transcriptional activation on the protein level in signal transduction imaging in live cells or animals.

Example 7

Fluorescence Resonance Energy Transfer in Near-Infrared Fluorescent Oligonucleotide Probes for Detecting Protein-DNA Interactions A fluorescence resonance energy transfer (FRET) reporter duplex design was selected that included a pair of near-infrared fluorochromes. The acceptor of fluorescence (Cy7 or 800CW) was linked via an amino group introduced close to the p50 binding sequence whereas the donor fluorochrome (Cy5.5) was linked to the 3'-end of the complementary ODN (FIG. 19A).

Conjugation of oligonucleotides bearing 3'-hydroxypropyldithiopropyl linkers with Cy5.5 maleimide was accomplished by dissolving 30 nmol of oligonucleotide in 100 µl 12 mM NaHCO$_3$. Eleven µL of 1 M DTT was added and the mixture was incubated for 1 hour at room temperature, followed by ethanol/acetate precipitation and dissolving in 160 µL 0.1 M sodium phosphate buffer, pH 7.5. Twenty µL of Cy5.5 maleimide (5 mg/ml DMSO) were added in two increments within a period of 1 hour. After reacting in the dark overnight, the labeled oligonucleotide was purified by spin-chromatography using BioSpin P6 microcolumns (Metelev et al., (2004) Bioconj Chem 15: 1481-1487), followed by reverse phase HPLC, and finally, by using ethanol/sodium acetate precipitation.

To conjugate fluorochromes to amino linkers, ten nmol of amino linker-bearing oligonucleotide were dissolved in 30 µl of 0.1 M NaHCO$_3$. Two 7.5 µl portions of dye solutions (0.5 mg Cy7 mono N-hydroxysuccinimide ester (NHS) or 800CW NHS in 30 µl DMSO) were added over a 1 hour interval, and the homogeneous reaction mixture was left overnight at room temperature in the dark. The labeled oligonucleotide was purified by P6 spin-chromatography followed by reverse phase HPLC column (Microsorb MV100 C18, Varian, Lake Forest Calif.) eluted using a linear gradient of 2-50% acetonitrile in 0.1 M TEAA, pH 7. ODNs were concentrated using ethanol/sodium acetate precipitation.

Five ODNs were synthesized, purified and tested for duplex formation (Tables 4 and 5). These ODNs included: 1) ODN1 bearing human beta2-microglobulin kappa B box sequence (5'-GGAAAGTCCC-3'; SEQ ID NO:8) (Gobin et al., (2003) Blood 101: 3058-3064), which was used primarily as a control for 2) ODN2 which had a novel internucleoside phosphate triethylene glycol amino linker positioned after the first thymidine within 5'-GGAAAGTCCC-3' (SEQ ID NO:8) binding sequence; ODN2 was used to prepare covalent conjugates with Cy7 and 800CW dyes; 3) complementary ODN3 that had a 3'-dithiopropyl linker for conjugating fluorochromes using corresponding maleimides; ODN3 was used to synthesize conjugates with Cy5.5; 4) ODN4 having a truncated NF-κB p50 binding site GGAAAG and internucleoside phosphate triethylene glycol amino linker positioned four bases downstream from the last guanine in the binding site; 5) a complementary ODN5 that was similar to ODN3 in that it also had a 3'-dithiopropyl linker. These ODNs were characterized by electrospray mass-spectrometry, which showed a good correlation between the calculated and observed m/z values (Table 4).

TABLE 4

Oligonucleotides and Conjugates

| ODN | # | Sequence | Mass-spec, m/z calculated | measured | Modification |
|---|---|---|---|---|---|
| ODN1 | | CGGAAAGTCCCTCATAGCT (SEQ ID NO: 1) | 5777.2 | 5771.6 | N/A |
| ODN2 | I | C**GGAAAGT\*CCC**TCATAGCT (SEQ ID NO: 1) | 5904.0 6888.9 | 5904.2 6888.0 (800CW) | CW800, Cy7 |
| ODN3 | | XIXAGCTATGAGGGACTTTCCGY (SEQ ID NO: 5) | 6087.9 7036.0 | 6087.6 7035.9 (Cy5.5) | 3'-Cy5.5 |
| ODN4 | II | TGGAAAGCTTTT\*TACAGTT (SEQ ID NO: 2) | 5964.0 6949.0 | 5964.4 6950.0 (800CW) | CW800, Cy7 |
| ODN5 | XX | AACTGTAAAAAGCTTTCCAY (SEQ ID NO: 7) | ND | | 3'-Cy5.5 |

T* is T-O-P((OH)=O)-OCH$_2$CH$_2$OCH$_2$CH$_2$OCH$_2$CH$_2$NH$_2$ for native form;
Y = HOCH$_2$CH$_2$SSCH$_2$CH$_2$CH$_2$O-(O=(HO))P-O-;
ND = not done The observed difference in masses between ODN1 and ODN2 pointed to the presence of an internucleoside phosphorus-linked (OCH$_2$CH$_2$)$_3$NH$_2$ group. The synthetically introduced linker groups were useful for high-yield linking of fluorochromes to ODNs. A comparison of internucleoside phosphate linkers to nucleic acid base-linked amino groups established that the latter were resulting in fluorochrome-linked products with 2.5-fold lower yields than the former (described in detail above).

The FRET between Cy5.5 and the acceptor on complementary ODN was observed after Cy5.5-ODN3 was incubated with Cy7- or 800CW-linked to ODN2 (see FIGS. 20A-B). The decrease of Cy5.5 emission and the increase of the acceptor emission were observed for all pairs of complementary ODNs and donor/acceptor pairs used in this study (FIGS. 20A-D). In the presence of internucleoside phosphate-linked Cy7 on the complementary strand it was observed more than 10 times lower fluorescence of Cy5.5 measured at 700 nm (λex=675 nm) and a 3-fold higher fluorescence of Cy7 (if compared to the duplex formed between Cy7-ODN2 and ODN3), FIGS. 20A-D. The formation of duplexes and reversible FRET effects were further studied in more detail by following sigmoidal dependence of the temperature-dependent increase of Cy5.5 fluorescence in a microcuvette of a spectrofluorometer. These experiments enabled measurement of two parameters: melting temperatures and the overall FRET efficacy (Table 5). In general, FRET efficacies were higher in the case of Cy5.5-Cy7 donor-acceptor pair than in the case of Cy5.5-800CW pair, particularly in the case of ODN4/ODN5 duplexes, which showed a 10% less efficient FRET efficiency if compared to the Cy5.5-Cy7 donor-acceptor pair (Table 5).

TABLE 5

Oligonucleotide duplexes and their properties

| Duplex | Duplex | Melting point, ° C, method | FRET efficiency |
|---|---|---|---|
| ODN1/ODN3 | 5'-CGG AAA GTC CCT CAT AGC T-3' (SEQ 1ID NO: 1)<br>3'- YGCC TTT CAG GGA GTA TCG A-5' (SEQ ID NO: 5) | 66 (UV) | N/A |
| ODN2/ODN3 | 5'-CGG AAA GT*C CCT CAT AGC T-3' (SEQ 1ID NO: 1)<br>3'-YGCC TTT CAG GGA GTA TCG A-5' (SEQ ID NO: 5) | 64 (UV) | N/A |
| 800CW-ODN2/ Cy5.5-ODN3 | 5'-CGG AAA GT$^{800CW}$C CCT CAT AGC T-3' (SEQ ID NO: 1)<br>3'-Cy5.5-S-GCC TTT CAG GGA GTA TCG A-5' (SEQ ID NO: 5) | 59 (FRET) | 82.9 ± 2.3 |
| Cy7-ODN2/ Cy5.5-ODN3 | 5'-CGG AAA GT$^{Cy7}$C CCT CAT AGC T-3' (SEQ ID NO: 1)<br>3'-Cy5.5-S-GCC TTT CAG GGA GTA TCG A-5' (SEQ ID NO: 5) | 59 (FRET) | 86.3 ± 3.0 |
| ODN4/ODN5 | 5'-TGG AAA GCT TTT* TAC AGT T-3' (SEQ ID NO: 2)<br>3'- YACC TTT CGA AAA ATG TCA A-5' (SEQ ID NO: 7) | 61 (UV) | N/A |
| 800CW-ODN4/Cy5.5-ODN5 | 5'-TGG AAA GCT TTT$^{800CW}$TAC AGT T-3' (SEQ ID NO: 2)<br>3'-Cy5.5-S-ACC TTT CGA AAA ATG TCA A-5' (SEQ ID NO: 7) | 55 (FRET) | 60.7 ± 1.1 |
| Cy7-ODN4/Cy5.5-ODN5 | 5'-TGG AAA GCT TTT$^{Cy7}$ TAC AGT T-3' (SEQ ID NO: 2)<br>3'-Cy5.5-S-ACC TTT CGA AAA ATG TCA (SEQ ID NO: 7) | 53 (FRET) | 71.8 ± 1.0 |

Y = HOCH$_2$CH$_2$SSCH$_2$CH$_2$CH$_2$O—(O=(HO))P—O—

ODN2/ODN3 duplexes (800CW-ODN2/Cy5.5-ODN3 and Cy7-ODN2/Cy5.5-ODN3) gave higher FRET efficacies than the corresponding donor-acceptor pairs in the case of ODN4/ODN5 duplexes (Table 5). Fluorescence spectral measurements confirmed this observation (compare FIGS. 20A-B and FIGS. 20C-D). The higher efficacy of FRET was a consequence of a more extensive overlap between the emission spectrum of Cy5.5 ($\lambda_{ex}$=675 nm) and the excitation spectrum of Cy7 donor than that of 800CW (FIG. 19B). The area of spectral overlap in the case of Cy5.5-Cy7 was 26% higher than in the case of Cy5.5-800CW donor-acceptor pairs (FIG. 19B). The measurements of melting points suggested a complete separation of ODNs with temperature increase and, consequently, the loss of FRET effect. Compared to ODN1/ODN3 and ODN2/ODN3 duplexes ODN4/ODN5 duplexes had lower melting temperature due to a higher A-T content (68% vs. 48%).

A small temperature shift was observed after the linking of fluorochrome pairs to the duplex-forming ODNs if compared to UV (260 nm) measurements performed using non-labeled ODN1-ODN3 duplex (Table 5). The measurements of spectral overlaps in Cy5.5-Cy7 and Cy5.5-800CW donor-acceptor pairs and FRET efficacies enabled estimations of the effective distances between the pairs of fluorochromes in different ODN duplexes. Cy7-ODN2/Cy5.5-ODN3 duplex (average FRET efficiency (E) was 86%) was 49.4 Å, the longest—64.7 Å—was measured in 800CW-ODN4/Cy5.5-ODN5 duplex (E=60.7%).

The binding of NF-κB p50 to duplexes was initially followed by using two methods: 1) electrophoretic mobility shift essay (EMSA) in polyacrylamide gels; 2) fluorescence energy transfer loss measurements after adding p50 to the duplex in solution. In the first case the components of the mixture are off equilibrium since the free duplex is separated due to a faster migration in electric field during the analysis. The second method afforded measurements at the equilibrium but the observed fluorescence change values are affected by the background fluorescence due to the presence of the free duplex. After resolving the reaction mixture on 10% polyacrylamide gels it was observed a typical fluorescence shift to the area close to the origin of electrophoresis, suggesting the formation of a high-molecular mass complex between p50 and the fluorescent duplex. Fluorescence of both free and bound duplex could be imaged by using a transillumination scanner and CCD camera that detected emitted light at two wavelengths—700 m (FIG. 21A) and 800 nm (FIG. 21B, fused image—FIG. 21C). Interestingly, both full-length (duplex 800CW-ODN2/Cy5.5-ODN3) and truncated p50 binding sites (duplex 800CW-ODN4/Cy5.5-ODN5) showed typical migration shifts (FIG. 21D). However, by comparing Cy5.5-labeled duplexes (ODN2/Cy5.5-ODN3 and ODN4/Cy5.5-ODN5) it was determined that in the case of full-length binding sites 94% of fluorescence co-migrated with p50, whereas only 63% co-migrated with ODN4/Cy5.5-ODN5 duplex (FIG. 21D) at the saturating concentrations of p50 monomer (200 nM). Recombinant p50 showed concentration-dependent binding that allowed semi-quantitative measurements of donor and acceptor fluorescence intensities (FIGS. 22A-B).

By measuring fluorescence intensities at various p50 concentrations using the excess of p50 at various concentrations (10-600 ng, 4-240 nM) at the constant duplex concentration (1.8 nM ODN1/Cy5.5-ODN3 duplex) it was determined that binding curves had sigmoidal shape, which suggests a strong cooperativity of p50-probe interaction with duplexes, consistent with the formation of p50 homodimer (p105)-ODN probe complexes (FIG. 22A). The half-maximal amount of p50 was 238-300 ng (corresponding to approximately 600 nM). The binding to the duplex resulted in a measurable change of Cy5.5 fluorescence in the bound duplex if compared to free duplex. Measuring the ratio of fluorescence intensities at 700 nm and 800 nm in the shifted band (protein-duplex complex) determined that in the case of Cy7-ODN2/Cy5.5-ODN3 the ratio (3.7±0.4) was significantly higher than that in the free ODN duplex (2.3±0.2, p=0.002), FIG. 22B. A similar trend was observed if 800CW dye was used as Cy5.5 fluorescence acceptor and the differences were also significant (p=0.02). While both types of fluorescent duplex probes, i.e., having a full-length NK-kB binding sequence (ODN2/ODN3) and a truncated binding sequence (ODN4/ODN5) showed electrophoretic shifting, there was no measurably significant fluorescence changes in EMSA bands in the case of ODN4/ODN5, for both Cy5.5-800CW and Cy5.5-Cy7 donor/acceptor pairs.

The above measurements of p50-mediated changes of FRET efficacy were validated by using spectral measurements. Fluorescence was excited using 685 m and 785 nm light, emulating a gel infrared imaging system. Comparing ratios of fluorescence intensities measured at 700 nm and 800 nm determined that the total lack of FRET in the presence of Exo III resulted in a 700/800 ratio of 4.5±0.1 in the case of Cy7-ODN2/Cy5.5-ODN3 and 5.6±0.3 in the case of Cy7-ODN4/Cy5.5-ODN5. The baseline FRET ratios in the absence of Exo III were at 1.8±0.4 and 3.6±0.2, respectively, i.e., in the range measured using EMSA gels.

Finally, the effect of p50 on protection of donor-acceptor interaction from the degradation of exonuclease was studied (FIG. 23). The addition of the 250-times molar excess of p50 protein (calculated as homodimer) to the solution of Cy7-ODN2/Cy5.5-ODN3 resulted in a measurable, small but overall significant increase of Cy5.5 fluorescence (106-109% increase at $\lambda ex=675/\lambda em=696$ nm). The addition of 1 unit of Exo III to this solution resulted in a gradual increase of fluorescence at 696 nm, i.e., the half-maximum of fluorescence was reached at $t_{1/2}=22.5$ minutes. In contrast, in the absence of p50 protein the increase was almost instantaneous (FIG. 23, solid line). The protection of Cy7-ODN3/Cy5.5-ODN4 by p50 was much less efficient since both in the presence and the absence of p50 Exo III-mediated degradation of the duplex showed almost no detectable differences in kinetics (FIG. 23).

These results suggest that FRET between a pair of near-infrared dyes is sensitive to protein binding to ODN sequence and can be used for detecting protein-DNA interactions directly. Routine optimization of donor and acceptor fluorochromes and their respective positions along the base pairs that constitute the binding site allows monitoring of transcription factor binding to DNA duplex or hairpin-like probes in live cells and, one expects, in living systems.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of structure (I):

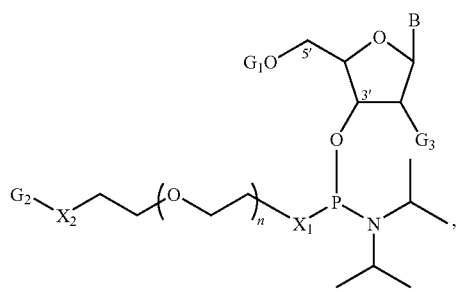

wherein $G_1$ is H or a hydroxyl protecting group;

B is a purine base residue, a pyrimidine base residue, a protected form of either base residue, or an analog of any of these;

$X_1$ is S or O;

n is an integer between 1 and 30, inclusive;

$X_2$ is NH;

$G_2$ is H, a protecting group or a moiety that includes a tag, a fluorochrome, a peptide, a polyethylene glycol moiety, or a quenching agent; and $G_3$ is a non-nucleophile and is selected from hydrogen, halogens, alkyl, hydroxyl, alkoxy, alkoxyethoxy, and t-butyldimethylsilyloxy.

2. The compound of claim 1, wherein $G_1$ is dimethoxytrityl (DMTr).

3. The compound of claim 1, wherein the B is a purine base residue or a protected form thereof.

4. The compound of claim 1, wherein the B is a pyrimidine base residue or a protected form thereof.

5. The compound of claim 1, wherein the B is one of B1, B2, B3, B4, or B5:

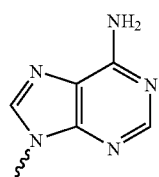

adenine residue

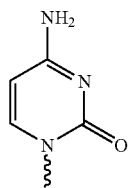

cytosine residue

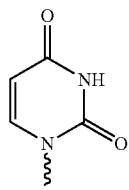

uracil residue

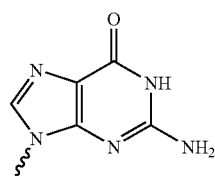

guanine residue

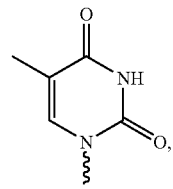

thymine residue or a protected form thereof.

6. The compound of claim 1, wherein $X_1$ is sulfur.

7. The compound of claim 1, wherein $X_1$ is oxygen.

8. The compound of claim 1, wherein n is an integer between 1 and 20, inclusive.

9. The compound of claim 1, wherein n is an integer between 2 and 10, inclusive.

10. The compound of claim 1, wherein $G_3$ is hydrogen.

11. The compound of claim 1, wherein $G_3$ is hydroxyl.

12. The compound of claim 1, wherein $G_2$ is hydrogen.

13. The compound of claim 1, wherein $G_2$ is trifluoroacetyl.

14. The compound of claim 1, wherein $G_2$ is a fluorochrome.

15. The compound of claim 1, wherein $G_2$ is a quenching agent.

16. The compound of claim 1, wherein $G_3$ is H, and $G_2$ is $CF_3C(=O)$.

17. The compound of claim 1, wherein $G_3$ and $G_2$ are both H.

18. The compound of claim 1, wherein $G_1$ is DMTr; B is B5 (thymine residue); $X_1$ is 0; n is 1, 2, 3, 4, or 5; $G_3$ is H, and $G_2$ is $CF_3C(=O)$.

19. An oligonucleotide comprising:

an oligonucleotide sugar-phosphate backbone;

a plurality of spaced apart bases, each bonded to a sugar unit of the sugar-phosphate backbone wherein the sugar unit is selected from a ribose sugar, a deoxyribose sugar, or an analog thereof; and at least one linker moiety bonded to a phosphorus atom of the sugar-phosphate backbone, wherein the linker moiety is bonded to an internucleotide phosphorus atom of the oligonucleotide sugar-phosphate backbone; the linker moiety comprising:

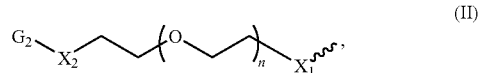

(II)

wherein $X_1$ is S or O;

n is an integer between 1 and 30, inclusive;

$X_2$ is NH; and $G_2$ is H, a protecting group or a moiety that includes a tag, a fluorochrome, a peptide, a polyethylene glycol moiety, or a quenching agent.

20. The oligonucleotide of claim 19, wherein n is an integer between 1 and 20, inclusive.

21. The oligonucleotide of claim 19, wherein n is an integer between 2 and 10, inclusive.

22. The oligonucleotide of claim 20, wherein $G_2$ is $CF_3C(=O)$.

23. The oligonucleotide of claim 19, wherein $G_2$ is H.

24. An oligonucleotide comprising:

an oligonucleotide sugar-phosphate backbone;

a plurality of spaced apart bases, each bonded to a sugar unit of the sugar-phosphate backbone wherein the sugar unit is selected from a ribose sugar, a deoxyribose sugar, or an analog thereof; and at least one linker moiety bonded to a phosphorus atom of the sugar-phosphate backbone, the linker moiety comprising:

(II)

wherein
X₁ is S or O;
n is an integer between 1 and 30, inclusive;
X₂ is NH; and
G₂ is any one of C1 to C4:

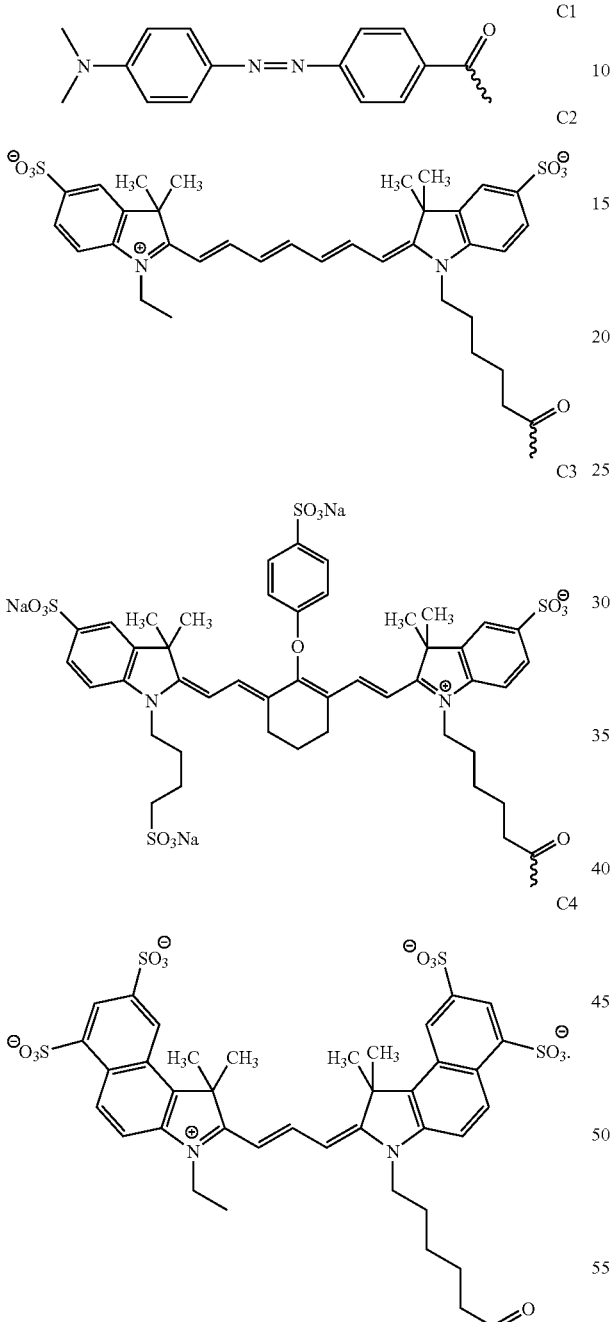

25. The oligonucleotide of claim 19, wherein the oligonucleotide is a oligodeoxyribonucleotide.
26. The oligonucleotide of claim 19, wherein the oligonucleotide is a oligoribonucleotide.
27. The oligonucleotide of claim 26, wherein the oligoribonucleotide is a small interfering oligoribonucleotide (siRNA).
28. The oligonucleotide of claim 26, wherein the oligoribonucleotide is a double stranded oligoribonucleotide (dsRNA).
29. The oligonucleotide of claim 26, wherein at least 50% of the phosphorus atoms of the sugar-phosphate backbone are bonded to a linker moiety.
30. A method of making an oligonucleotide having a linker moiety, the method comprising
  selecting an oligonucleotide comprising an oligonucleotide sugar-phosphate backbone having a plurality of spaced apart bases, each bonded to a sugar unit of the sugar-phosphate backbone, the sugar unit including a free hydroxyl group at the 5' position; and
  reacting a compound of Structure (I) with the selected oligonucleotide in a manner that the phosphorus atom of Structure (I) is bonded to the 5' oxygen atom of the oligonucleotide sugar-phosphate backbone to provide an oligonucleotide having a linker moiety, the compound of structure (I) being:

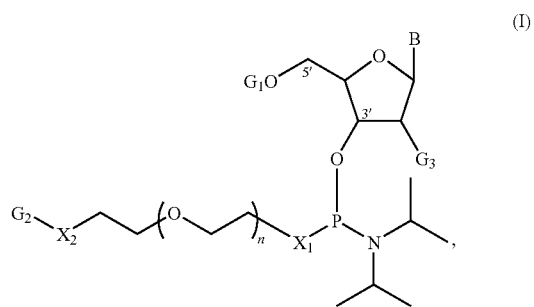

wherein
  G₁ is H or a hydroxyl protecting group;
  B is a purine base residue, a pyrimidine base residue, a protected form of either base residue, or an analog of any of these;
  X₁ is S or O;
  n is an integer between 1 and 30, inclusive;
  X₂ is NH;
  G₂ is H, a protecting group or a moiety that includes a tag, a fluorochrome, a peptide, a polyethylene glycol moiety, or a quenching agent; and
  G₃ is a non-nucleophile and is selected from hydrogen, halogens, alkyl, alkoxy, alkoxyethoxy, and t-butyldimethylsilyloxy.
31. A method of delivering an oligonucleotide into a cell, the method comprising:
  incubating the oligonucleotide with the cell, the oligonucleotide comprising:
    an oligonucleotide sugar-phosphate backbone; and
    a linker moiety bonded to a phosphorus atom of the sugar-phosphate backbone, wherein the linker moiety is bonded to an internucleotide phosphorus atom of the oligonucleotide sugar-phosphate backbone; the linker moiety comprising:

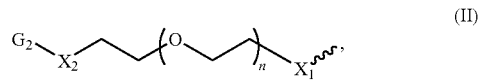

wherein

X₁ is S or O;

n is an integer between 1 and 30, inclusive;

X₂ is NH; and

G₂ is H, a protecting group or a moiety that includes a tag, a fluorochrome, a peptide, a polyethylene glycol moiety, or a quenching agent.

32. The method of claim 31, wherein G2 is a fluorochrome.

33. The method of claim 31, wherein G2 is a quenching agent.

34. The method of claim 31, wherein X₁ is O; and G₂ is a fluorochrome.

35. The method of claim 31, wherein the oligonucleotide has at least 5% of the phosphorus atoms of the sugar-phosphate backbone bonded to a linker moiety.

36. The method of claim 31, wherein the oligonucleotide is a duplex oligonucleotide.

37. The method of claim 31, wherein the cell is an endothelial cell.

38. A method of detecting a duplex oligonucleotide-protein interaction, the method comprising:

contacting a protein with a duplex of oligonucleotides of claim 19, wherein each of the oligonucleotides comprises a fluorochrome that can participate in fluorescence resonance energy transfer (FRET);

measuring a fluorescence property of the oligonucleotides in the absence of the protein;

measuring a fluorescence property of the oligonucleotides in the presence of the protein; and comparing the fluorescence property of the oligonucleotides in the absence of the protein with the fluorescence property of the oligonucleotides in the presence of the protein, wherein a difference in the fluorescence properties indicates an interaction between the duplex oligonucleotide and protein.

39. The method of claim 38, wherein the protein is in a living cell.

40. The compound of claim 1, wherein G₂ is any one of C1 to C4:

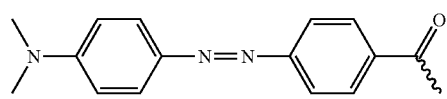

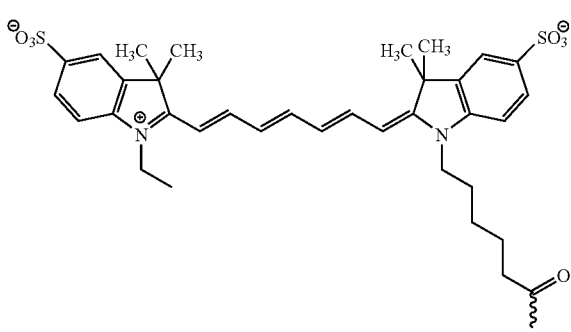

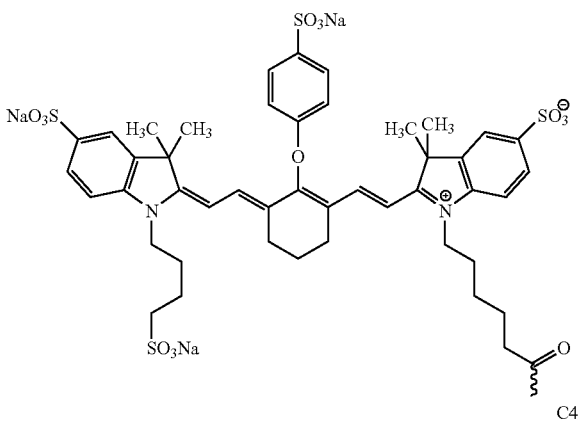

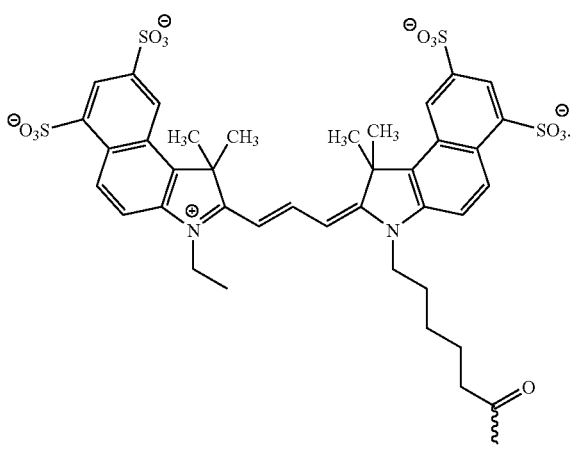

41. A compound of structure (I):

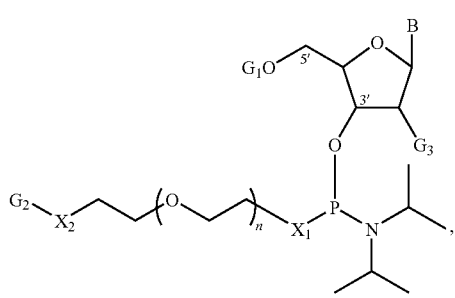

wherein

G₁ is H or a hydroxyl protecting group;

B is a purine base residue, a pyrimidine base residue, a protected form of either base residue, or an analog of any of these;

X₁ is S;

n is an integer between 1 and 30, inclusive;

X₂ is O, S or NH;

G₂ is H, a protecting group or a moiety that includes a tag, a fluorochrome, a peptide, a polyethylene glycol moiety, or a quenching agent; and G₃ is a non-nucleophile and is selected from hydrogen, halogens, alkyl, hydroxyl, alkoxy, alkoxyethoxy, and t-butyldimethylsilyloxy.

42. The compound of claim 41, wherein $G_1$ is dimethoxytrityl (DMTr).

43. The compound of claim 41, wherein the B is a purine base residue or a protected form thereof.

44. The compound of claim 41, wherein the B is a pyrimidine base residue or a protected form thereof.

45. The compound of claim 41, wherein n is an integer between 2 and 10, inclusive.

46. The compound of claim 41, wherein $G_3$ is hydrogen.

47. The compound of claim 41, wherein $G_2$ is trifluoroacetyl.

48. The compound of claim 41, wherein $G_2$ is a fluorochrome.

49. The compound of claim 41, wherein $G_2$ is a quenching agent.

* * * * *

UNITED STATES PATENT AND TRADEMARK OFFICE
CERTIFICATE OF CORRECTION

PATENT NO. : 8,084,589 B2
APPLICATION NO. : 12/201758
DATED : December 27, 2011
INVENTOR(S) : Alexei Bogdanov et al.

It is certified that error appears in the above-identified patent and that said Letters Patent is hereby corrected as shown below:

Col. 1, Lines 14-20, delete "This invention was made with Government support under Grant Nos. R01 AI060872, awarded by the National Institute of Allergy and Infectious Diseases, R21 CA116144, awarded by the National Cancer Institute, and R01 EB000858, awarded by the National Institute of Biomedical Imaging and Bioengineering. The Government has certain rights in the invention." and insert --This invention was made with Government support under Grant Nos. R01 AI060872, awarded by the National Institute of Allergy and Infectious Diseases, National Institutes of Health, R21 CA116144, awarded by the National Cancer Institute, National Institutes of Health, and R01 EB000858, awarded by the National Institute of Biomedical Imaging and Bioengineering, National Institutes of Health. The Government has certain rights in the invention.--, therefor.

Col. 44, Line 12, In claim 18, delete "0;" and insert --O;--, therefor.

Col. 47, Line 14, In claim 34, delete "0;" and insert --O;--, therefor.

Signed and Sealed this
Sixth Day of March, 2012

David J. Kappos
*Director of the United States Patent and Trademark Office*